United States Patent

Ksander

(10) Patent No.: US 6,878,707 B2
(45) Date of Patent: Apr. 12, 2005

(54) CARBOXAMIDES USEFUL AS INHIBITORS OF MICROSOMAL TRIGLYCERIDE TRANSFER PROTEIN AND OF APOLIPOPROTEIN B SECRETION

(75) Inventor: Gary Michael Ksander, Milford, NJ (US)

(73) Assignee: Novartis AG, Basel (CH)

(*) Notice: Subject to any disclaimer, the term of this patent is extended or adjusted under 35 U.S.C. 154(b) by 299 days.

(21) Appl. No.: 10/181,006

(22) PCT Filed: Jan. 16, 2001

(86) PCT No.: PCT/EP01/00439

§ 371 (c)(1),
(2), (4) Date: Jul. 11, 2002

(87) PCT Pub. No.: WO01/53260

PCT Pub. Date: Jul. 26, 2001

(65) Prior Publication Data

US 2003/0109700 A1 Jun. 12, 2003

(51) Int. Cl.[7] ............... C07D 211/44; C07D 213/82; C07D 295/20; A61P 31/44; A61P 3/06

(52) U.S. Cl. ............ 514/237.8; 544/389; 544/400; 544/392; 544/166; 544/383; 544/360; 514/255.01; 514/255.03; 514/319; 514/278; 514/255.02; 514/253.01; 546/205; 546/19

(58) Field of Search ............... 544/389, 400, 544/392, 166, 383, 360; 514/255.01, 255.03, 237.8, 319, 278, 255.02, 253.01

(56) References Cited

U.S. PATENT DOCUMENTS

| | | | |
|---|---|---|---|
| 5,053,430 A | 10/1991 | Grauert et al. | 514/630 |
| 5,597,826 A | 1/1997 | Howard et al. | 514/255 |
| 5,675,024 A | 10/1997 | Teng et al. | 549/405 |
| 5,919,795 A | 7/1999 | Chang et al. | 514/310 |
| 5,936,000 A | 8/1999 | Romero et al. | 514/647 |
| 5,958,927 A | 9/1999 | Peglion et al. | 514/254 |
| 5,998,623 A | 12/1999 | Urban | 546/143 |
| 6,197,798 B1 | 3/2001 | Fink et al. | 514/354 |

FOREIGN PATENT DOCUMENTS

| | | |
|---|---|---|
| EP | 701 819 A2 | 3/1996 |
| WO | WO 95/04713 | 2/1995 |
| WO | WO 96/21640 | 7/1996 |
| WO | WO 96/36596 | 11/1996 |
| WO | WO 97/19052 | 5/1997 |
| WO | WO 97/24116 | 7/1997 |
| WO | WO 98/04521 | 2/1998 |
| WO | WO 98 23593 A | 6/1998 |
| WO | WO 00 05201 A | 2/2000 |
| WO | WO 00 32582 A | 6/2000 |
| WO | WO 00/32582 | 6/2000 |
| WO | WO 01 05767 A | 1/2001 |

Primary Examiner—John M. Ford
Assistant Examiner—Hong Liu
(74) Attorney, Agent, or Firm—Norbert Gruenfeld; Paivi Kukkola

(57) ABSTRACT

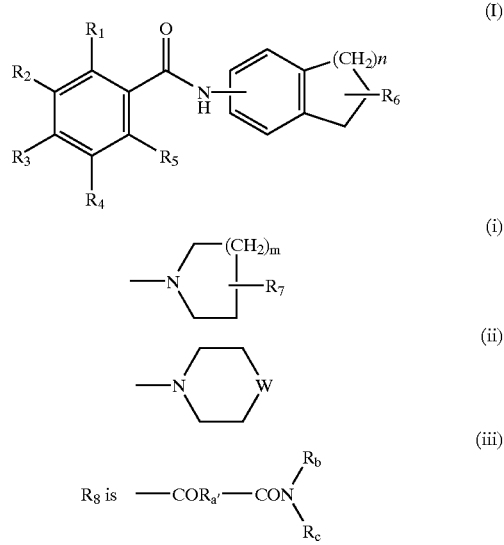

Compounds of formula (I) wherein $R_2$—C, $R_3$—C, $R_4$—C or $R_5$—C may be replaced by N; and wherein n is 1, 2 or 3; $R_1$ is aryl, heteroaryl or (aryl or heteroaryl)-lower alkoxy; $R_2$, $R_3$, $R_4$ and $R_5$ are independently hydrogen, lower alkyl, lower alkoxy, halo, trifluoromethyl or cyano; $R_6$ is (i) or (ii) m is 1, 2 or 3; $R_7$ is hydrogen, lower alkyl (aryl or heteroaryl)-lower alkyl, lower alkoxy, (aryl or heteroaryl)-lower alkoxy, hydroxy, oxo, lower alkylenedioxy or lower alkanoyloxy; W is O, S or $NR_8$; $R_8$ is —$COR_a$, (iii), —$COOR_d$, —$SO_2R_e$, hydrogen, optionally substituted lower alkyl, aryl, heteroaryl or (aryl or heteroaryl)-lower alkyl; $R_a$, $R_d$ and $R_e$ are independently optionally substituted lower alkyl, cycloalkyl, adamantyl, aryl, heteroaryl or (aryl or heteroaryl)-lower alkyl; $R_b$ and $R_c$ are independently hydrogen, cycloalkyl, optionally substituted lower alkyl, aryl, heteroaryl or (aryl or heteroaryl) lower alkyl; or $R_b$ and $R_c$ together represent lower alkylene; and pharmaceutically acceptable salts thereof; and enantiomers thereof; which are useful as inhibitors of microsomal triglyceride transfer protein (MTP) and of apolipoprotein B (apoB) secretion.

14 Claims, No Drawings

CARBOXAMIDES USEFUL AS INHIBITORS OF MICROSOMAL TRIGLYCERIDE TRANSFER PROTEIN AND OF APOLIPOPROTEIN B SECRETION

This application claims the benefit of provisional application No. 60/304,201 filed Jan. 18, 2000 which was converted from application Ser. No. 09/483,971.

The invention relates to the compounds of formula I

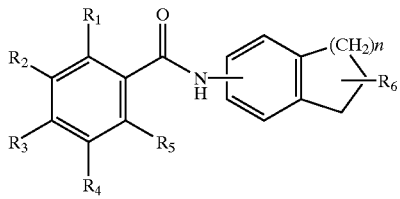

wherein $R_2$—C, $R_3$—C, $R_4$—C or $R_5$—C may be replaced by N;
and wherein n is 1, 2 or 3;
$R_1$ is aryl, heteroaryl or (aryl or heteroaryl)-lower alkoxy;
$R_2$, $R_3$, $R_4$ and $R_5$ are independently hydrogen, lower alkyl, lower alkoxy, halo, trifluoromethyl or cyano;
$R_6$ is

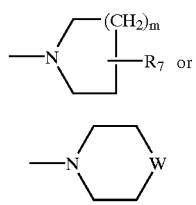

m is 1, 2 or 3;
$R_7$ is hydrogen, lower alkyl, (aryl or heteroaryl)-lower alkyl, lower alkoxy, (aryl or heteroaryl)-lower alkoxy, hydroxy, oxo, lower alkylenedioxy or lower alkanoyloxy;
W is O, S or $NR_8$;
$R_8$ is —$COR_a$,

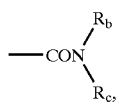

—$COOR_d$, —$SO_2R_e$, hydrogen, optionally substituted lower alkyl, aryl, heteroaryl or (aryl or heteroaryl)-lower alkyl;
$R_a$, $R_d$ and $R_e$ are independently optionally substituted lower alkyl, cycloalkyl, adamantyl, aryl, heteroaryl or (aryl or heteroaryl)-lower alkyl;
$R_b$ and $R_c$ are independently hydrogen, cycloalkyl, optionally substituted lower alkyl, aryl, heteroaryl or (aryl or heteroaryl) lower alkyl; or $R_b$ and $R_c$ together represent lower alkylene;
and pharmaceutically acceptable salts thereof; and enantiomers thereof.

Compounds of formula I are useful as inhibitors of microsomal triglyceride transfer protein (MTP) and of apolipoprotein B (apoB) secretion and accordingly for the treatment of MTP and apo B dependent conditions.

A particular embodiment of the invention relates to the compounds of formula I'

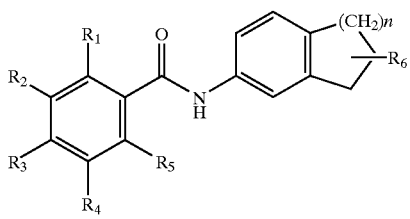

wherein $R_2$—C, $R_3$—C, $R_4$—C or $R_5$—C may be replaced by N; and wherein n, and $R_1$-$R_6$ have meaning as defined above; pharmaceutically acceptable salts thereof; and enantiomers thereof.

A specific embodiment of the invention relates to the compounds of formula Ia

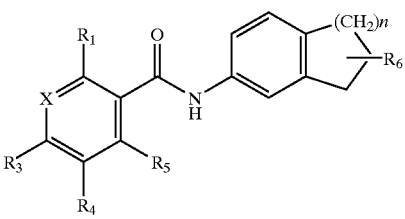

wherein X is $R_2$—C or N; and n, and $R_1$-$R_6$ have meaning as defined above; pharmaceutically acceptable salts thereof; and enantiomers thereof.

Preferred are the compounds of formula Ia wherein n is 1; $R_1$ is monocyclic aryl or heteroaryl; X is $R_2$—C or N; $R_2$, $R_3$, $R_4$ and $R_5$ are independently hydrogen, lower alkyl, halo, trifluoromethyl, lower alkoxy or cyano; $R_6$ is as defined above; pharmaceutically acceptable salts thereof; and enantiomers thereof.

A particular aspect of the invention relates to the indane derivatives of formula Ib

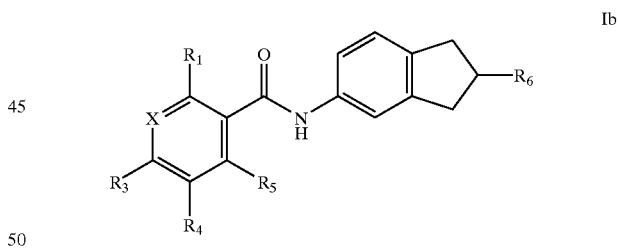

wherein $R_1$ is monocyclic aryl or heteroaryl;
X is $R_2$—C or N;
$R_2$, $R_3$, $R_4$ and $R_5$ are independently hydrogen, lower alkyl, halo, trifluoromethyl, cyano, or lower alkoxy;
and $R_6$ has meaning as defined above;
and pharmaceutically acceptable salts thereof; and enantiomer thereof.

Preferred are the said compounds of formula Ib wherein $R_1$ is phenyl or phenyl substituted by fluoro, chloro, trifluoromethyl, cyano or lower alkyl; X is N or $R_2$—C; $R_2$, $R_3$, $R_4$ and $R_5$ are independently hydrogen, lower alkyl, halo or trifluoromethyl; and $R_6$ has meaning as defined above; and pharmaceutically acceptable salts thereof; and enantiomers thereof.

Particular aspects of the invention relate to the compounds of the formulae I, I', Ia, Ib or Ib' wherein $R_6$ is group of formula (i) wherein $R_7$ is (aryl or heteroaryl)-lower alkyl, lower alkoxy, (aryl or heteroaryl)-lower alkoxy, hydroxy, lower alkanoyloxy, oxo or lower alkylenedioxy, and m is 2; or $R_6$ is group of formula (ii) wherein
W is $NR_8$; and $R_8$ is —$COR_a$,

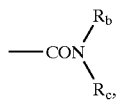

—$COOR_d$, or —$SO_2R_e$; and $R_a$–$R_e$ have meaning as defined above; pharmaceutically acceptable salts thereof; and enantiomers thereof.

Preferred are the compounds of formula Ia and Ib wherein X is $R_2$—C.

Further preferred are the compounds of formula Ic

Ic

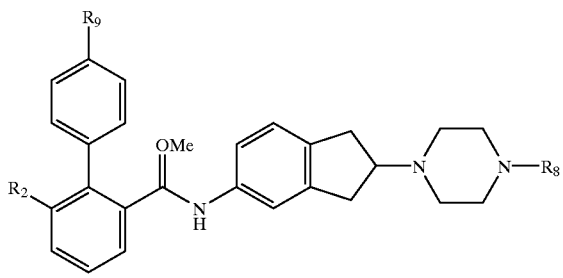

wherein $R_2$ is hydrogen, $C_1$–$C_4$-alkyl, $C_1$–$C_4$-alkoxy, trifluoromethyl, chloro or fluoro;
$R_8$ is —$COR_a$,

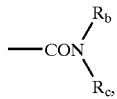

—$COOR_d$ or —$SO_2R_e$; $R_a$–$R_c$ have meaning as defined above;
$R_9$ is trifluoromethyl, chloro or cyano;
pharmaceutically acceptable salts thereof; and enantiomers thereof.

Further preferred are the compounds of formula Ic wherein $R_2$ is hydrogen, methyl or trifluoromethyl; $R_8$ is as defined above; $R_9$ is trifluoromethyl or chloro; pharmaceutically acceptable salts thereof; and enantiomers thereof.

A particular embodiment relates to the compounds of formula Ic wherein $R_2$ is methyl; $R_8$ is —$COOR_d$ wherein $R_d$ is lower alkyl; and $R_9$ is trifluoromethyl; pharmaceutically acceptable salts thereof; and enantiomers thereof.

Listed below are definitions of various terms used to describe the compounds of the instant invention. These definitions apply to the terms as they are used throughout the specification (unless they are otherwise limited in specific instances either individually or as part of a larger group).

The term "alkyl" refers to straight or branched chain hydrocarbon groups having 1 to 20 carbon atoms, preferably lower alkyl of 1 to 7 carbon atoms. Exemplary alkyl groups include methyl, ethyl, propyl, isopropyl, n-butyl, t-butyl, isobutyl, pentyl, hexyl, isohexyl, heptyl, 4,4-dimethylpentyl, octyl and the like.

The term "optionally substituted alkyl" refers to alkyl groups optionally substituted by e.g. one or more of the following groups: halo, $CF_3$, hydroxy, alkoxy, alkoxyalkoxy, aryloxy, cycloalkyl, alkanoyl, alkanoyloxy, amino, substituted amino, alkanoylamino, thiol, alkylthio, and the like.

The term "alkylene" referes to a straight chain bridge of 1 to 6 carbon atoms connected by single bonds (e.g., —$(CH_2)_x$— wherein x is 1 to 6) which may be substituted with 1 to 3 lower alkyl groups.

The term "lower alkyl" refers to those alkyl groups as described above having 1 to 7, preferably 1 to 4 carbon atoms.

The term "cycloalkyl" refers to cyclic hydrocarbon groups of 3 to 8 carbon atoms, such as cyclopentyl, cyclohexyl or cycloheptyl.

The term "adamantyl" refers to 1- or 2-adamantyl, preferably 1-adamantyl.

The term "halogen" or "halo" refers to fluorine, chlorine, bromine and iodine.

The term "alkoxy" or "alkyloxy" refers to alkyl-O—.

The term "aryl" or "ar" refers to carbocyclic monocyclic or bicyclic aromatic hydrocarbon groups having 6 to 12 carbon atoms in the ring portion, such as phenyl, naphthyl, tetrahydronaphthyl, and biphenyl groups, each of which may optionally be substituted by one to four substituents such as alkyl, halo, trifluoromethyl, hydroxy, alkoxy, alkanoyl, alkanoyloxy, amino, substituted amino, alkanoylamino, thiol, alkylthio, nitro, cyano, carboxy, carboxyalkyl, carbamyl, alkoxycarbonyl, alkylthiono, alkylsufonyl, aminosulfonyl, and the like.

The term "aralkyl" refers to an aryl group linked to an alkyl group, such as benzyl.

The term "heteroaryl" "or heteroar" refers to an aromatic heterocycle, for example monocyclic or bicyclic heterocyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl, and the like, optionally substituted by e.g., lower alkyl, lower alkoxy or halo, the point of attachment of said heterocycle being at a carbon atom of the heterocyclic ring.

Pharmaceutically acceptable salts of the compounds of the invention are particularly acid addition salts, such as of mineral acids, organic carboxylic, and organic sulfonic acids e.g., hydrochloric acid, methanesulfonic acid, maleic acid, and the like provided a basic group, such as pyridyl, constitutes part of the structure.

The compounds of the invention depending on the nature of the substituents, possess one or more asymmetric carbon atoms, and therefore exist as racemates and the (R) and (S) enantiomers thereof. All are within the scope of the invention. Preferred is the more active enantiomer typically assigned the R-configuration (at the carbon bearing the $R_6$ substituent). Illustrative thereof are the compounds of formula Ib (the R-isomers of the compound of formula Ib).

Ib'

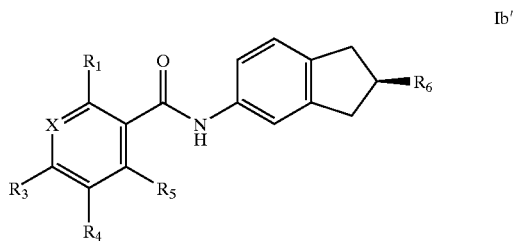

wherein $R_1$ is monocyclic aryl or heteroaryl;
X is $R_2$—C or N;
$R_2$, $R_3$, $R_4$ and $R_5$ are independently hydrogen, lower alkyl, halo, trifluoromethyl, cyano, or lower alkoxy;

and $R_6$ has meaning as defined above;
and pharmaceutically acceptable salts thereof.

Preferred are the compounds of formula Ib' wherein X is $R_2C$.

The compounds of the invention, as illustrated for representative compounds of formula Ib wherein $R_6$ is a group of formula (ii), can be prepared by e.g.

(a) condensing a compound of the formula

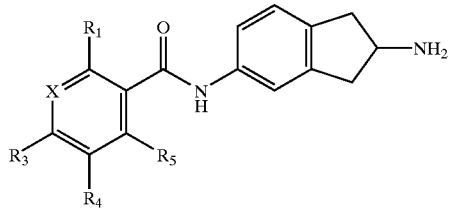

V with e.g. a compound of the formula

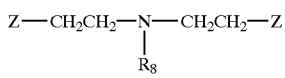

wherein $R_8$ is a group that serves as an N-protecting group, e.g. —$COOR_d$ or $SO_2R_e$, and Z is a leaving group such as halo (e.g. chloro) or alkylsulfonyloxy (e.g. methylsulfonyloxy), in the presence of a base; and, if appropriate, converting a compound so obtained to another compound of the invention; or (b) condensing a ketone of the formula

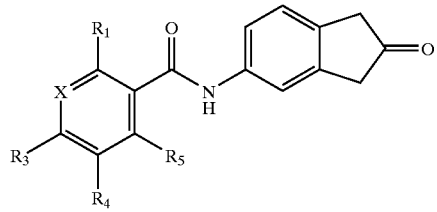

(B)

wherein symbols have meaning as defined above, with e.g. an amine of the formula

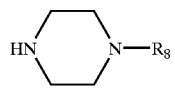

(C)

wherein $R_8$ has meaning as defined above, under conditions of reductive amination; and, if appropriate, converting a compound so obtained into another compound of the invention.

The processes can be carried out according to methodology well known in the art for the transformation involved, and illustrated in the example. For example, reductive amination of process (b) is carried out in the presence of e.g. sodium borohydride, sodium triacetoxyborohydride or polymer supported borohydride.

The condensation according to process (a) can be carried out in the presence of a tertiary amine, such as diisopropylethylamine, N-methylmorpholine, triethylamine or pyridine, optionally in the presence of an inert solvent such as methylene chloride.

A resulting compound wherein $R_8$ is arylsulfonyl, e.g. tosyl or lower alkoxycarbonyl (e.g. methoxycarbonyl) can be deprotected to a compound wherein $R_8$ is hydrogen by treatment with, e.g. HBr in acetic acid, optionally in the presence of phenol. Compounds wherein $R_8$ is hydrogen can in turn be converted to other compounds of the invention by treatment with the appropriate alkylating or acylating agent, for example an appropriately substituted sulfonyl chloride, carboxylic acid chloride or anhydride, carbonic acid chloride, carbamoyl chloride or isocyanate.

The amine starting material for process (a) can be prepared by coupling a protected compound of e.g. formula II

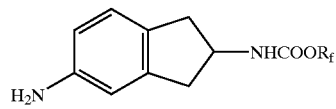

II wherein $R_f$ is lower alkyl,
with a reactive functional carboxylic acid derivative, e.g, a compound of formula III

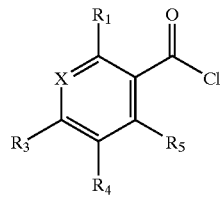

III wherein $R_1-R_5$ and X have meaning as defined above, in the presence of a base such as N-methylmorpholine, diisopropylethylamine, triethylamine or pyridine to provide compounds of the formula IV

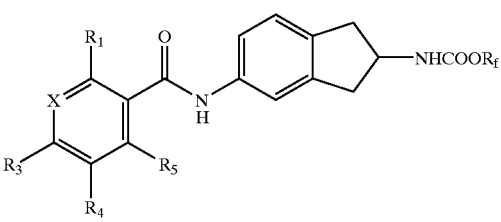

IV

Compounds of formula IV are then deprotected with an acid such as $HCO_2H$ or with trimethylsilyl iodide, to form compounds of formula V

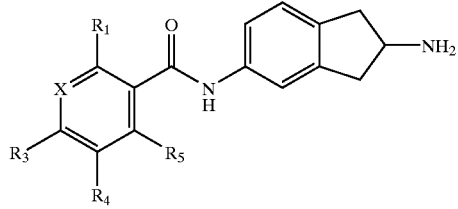

V

Intermediates of formula II are prepared e.g. by acid hydrolysis of N-(5-nitro-indan-2-yl)acetamide followed by protection of the resulting amine with t-BOC-anhydride and subsequent reduction, e.g., by catalytic hydrogenation, of the nitro group.

The biarylcarboxylic acids corresponding to the compounds of formula III can be prepared e.g. as described in Bioorg. Med. Chem. Lett. 7 (13), 1595 (1997).

Compounds of formula III wherein $R_1$ is aryl or heteroaryl can be prepared as illustrated in the scheme below by palladium catalyzed aryl-aryl coupling of aryl boronic acids of formula VI with bromo, iodo or trifluomethylmethanesulfonyloxy-substituted arylcarboxylic acid esters of e.g. formula VII. Subsequent hydrolysis of the ester group of resulting compounds of formula VIII with sodium hydroxide followed by reaction with a chlorinating agent such as oxalyl chloride gives acid chlorides of formula III.

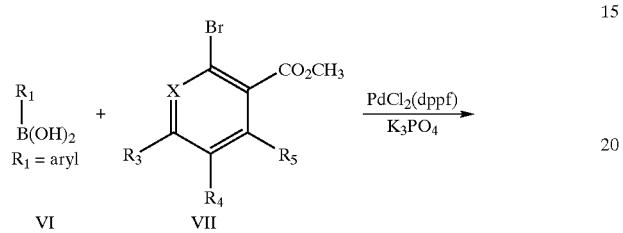

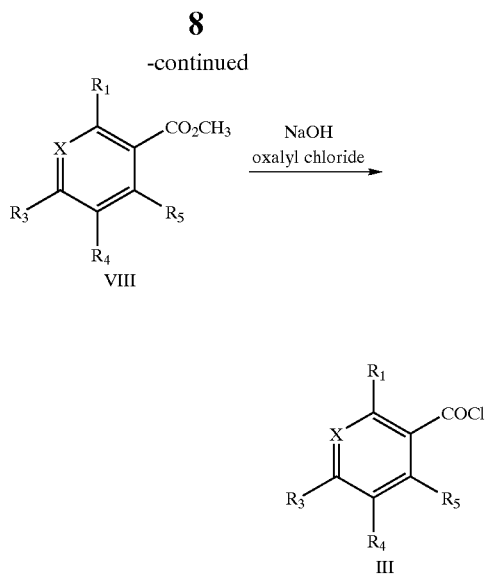

Compounds of formula V may also be prepared using the alternative synthesis below:

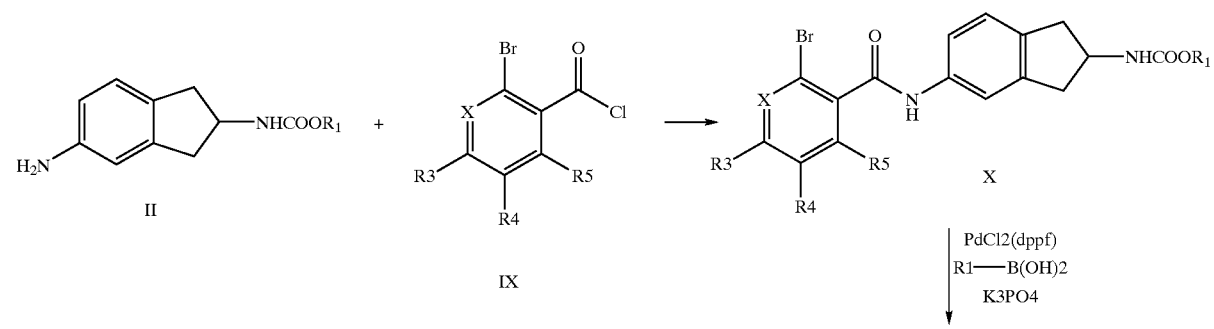

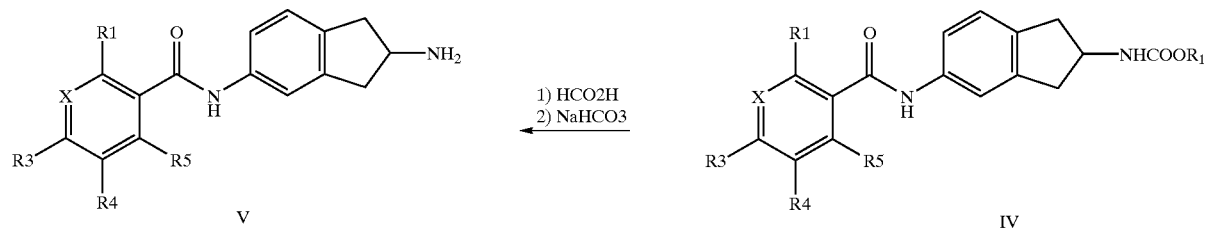

As shown above, amines of formula II are acylated with compounds of formula IX in the presence of a base such as N-methylmorpholine, diisopropylethylamine or pyridine to give compounds of the formula X. Palladium catalyzed aryl-aryl coupling of aryl boronic acids of formula ($R_1$-B(OH)$_2$) with aryl bromides of the formula X (or iodides or triflates) gives compounds of formula IV. Treatment with e.g. formic acid or trimethylsilyl iodide readily deprotects the nitrogen to give compounds of formula V.

The ketone starting materials for process (b) can be prepared as illustrated in the scheme below, starting from 2-hydroxyindane.

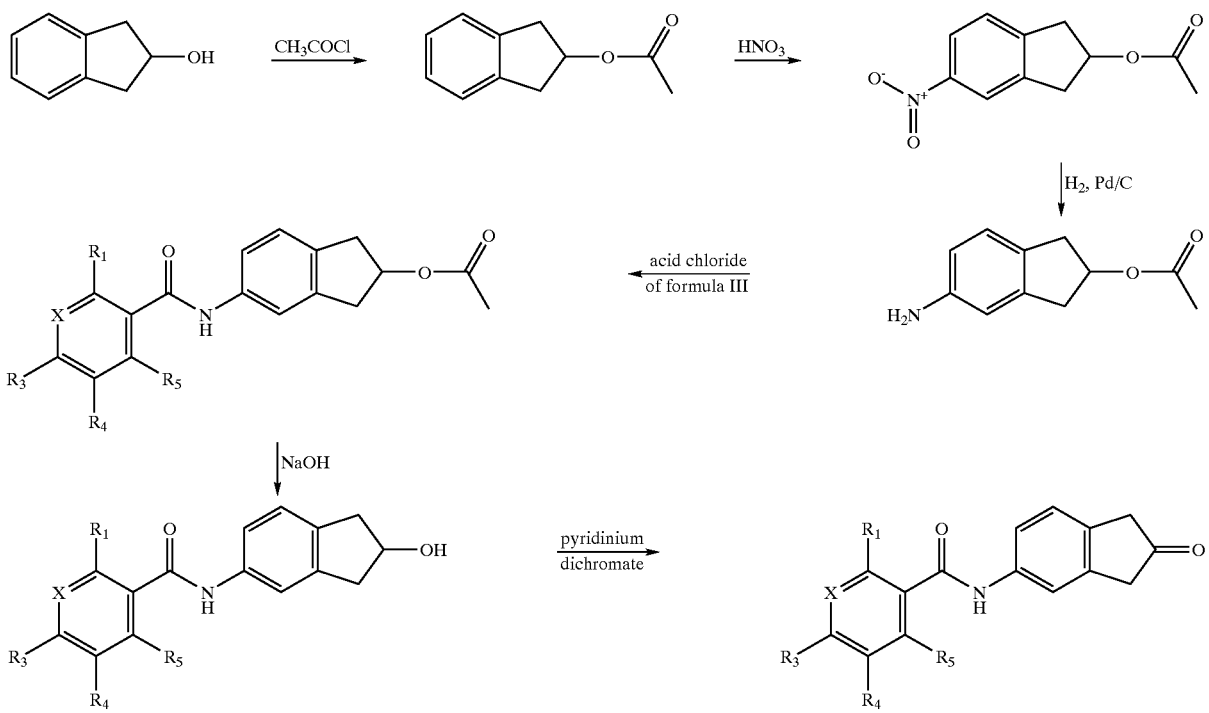

Chiral compounds of the invention can be prepared from chiral intermediates as follows:

(a) reducing (1S-trans)- or (1R-trans)-hydroxy-2-amino-6-nitroindane wherein the amino group is in protected form to the corresponding (R) or (S)-enantiomer of 2,6-diaminoindane in which the 2-amino group is in protected form;

(b) condensing said (R) or (S) enantiomer with a reactive derivative of a carboxylic acid, e.g., a compound of formula III, and removing the amino protecting group to obtain the (R) or (S) enantiomer of a compound of formula V; and (c) subsequently N-derivatizing a said enantiomer to a compound of the invention.

For example, chiral compounds of the invention, can be prepared e.g., by acylating a protected amine of e.g. formula XI

XI

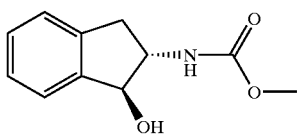

with acetyl chloride to form compounds of formula XII

XII

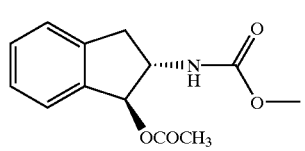

Compounds of formula XII are nitrated with nitric acid, trifluoroacetic acid and trifluoroacetic anhydride to form compounds of formula XIII

XIII

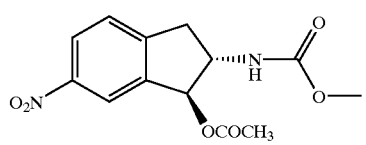

Compounds of formula XIII are saponified with sodium hydroxide to form compounds of formula XIV

XIV

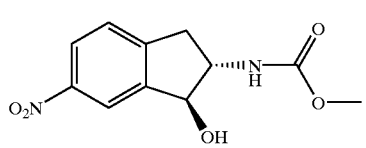

Compounds of formula XIV are reduced with hydrogen in the presence of Pd/C catalyst to form compounds of formula XV

XV

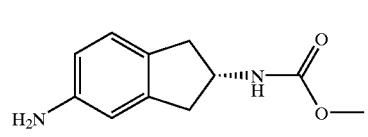

A compound of the formula XV is then coupled with a compound of formula III in the presence of a base such as N-methylmorpholine, diisopropylethylamine, triethylamine, or pyridine to provide e.g. a compound of formula XVI

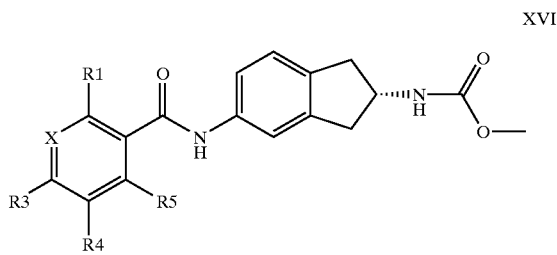

Compounds of formula XVI are then treated with e.g., trimethylsilyl iodide to form the chiral compounds of the formula V'

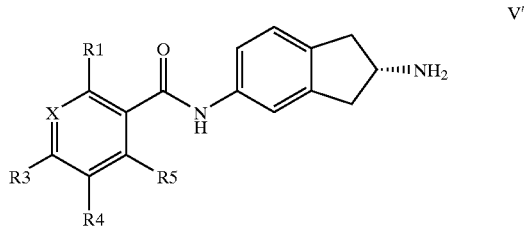

Amines of formula V' are then reacted as previously described to obtain the enantiomers corresponding to the compounds of formula Ib.

The opposite enantiomers are similarly prepared.

Alternatively, e.g. 5-bromo-2-aminoindane is resolved with D- or L-camphorsulfonic acid, and the resulting chiral amine is protected as e.g. the N-methoxycarbonyl derivative. Reaction with benzophenone imine (in a Buchwald condensation, Tetrahedron Letters 36. 6367, 1997) yields the corresponding chiral compound of formula XV (or its enantiomer).

A method for the preparation of enantiomers of the compounds of the invention, e.g. of formula Ib', thus comprises:
(1) resolving 5-bromo-2-aminoindane with either (R) or (S)-10-camphorsulfonic acid to obtain either chiral (R)- or (S)-5-bromo-2-aminoindane;
(2) protecting the resulting (R)- or (S)-5-bromo-2-aminoindane with e.g. an N-alkoxycarbonyl protecting group;
(3) reacting a said N-alkoxycarbonyl-5-bromo-2-aminoindane with benzophenone imine under conditions of a Buchwald condensation;
(4) cleaving the resulting 5-benzophenoneimine derivative by catalytic hydrogenation or treatment with acid;
(5) condensing the resulting 2-protected amino-5-aminoindane with a reactive derivative of a carboxylic acid, e.g. of the formula III wherein $R_1$, $R_3$–$R_5$ have meaning as defined herein, and optionally removing the amino protecting group to obtain the corresponding (R) or (S) enantiomer of a compound of formula V; and
(6) N-derivatizing a said compound according to process (a) above to obtain a compound of the invention.

(R)-2-Amino-5-bromoindane can be prepared e.g. by treating racemic 2-amino-5-bromoindane with 1(S)-10-camphorsulfonic acid, selectively crystallizing and purifying the resulting (R,S) diastereomeric salt, and then liberating, by treatment with a base, (R)-2-amino-5-bromoindane which is substantially free of the (S)-isomer.

In turn, racemic 2-amino-5-bromoindane is prepared by bromination of 2-aminoindane which is commercially available or is prepared by converting ninhydrin to 1,3-dioxo-2-hydroxyiminoindane followed by catalytic hydrogenation.

The Buchwald amination by condensation of e.g. 5-bromo-2-carbomethoxyaminoindane with benzophenone imine can be carried out similarly to the procedures described in Tetrahedron Letters 38, 6367 (1997). The amination is carried out in the presence of a palladium catalyst, a ligand and a base in an inert solvent such as toluene. Palladium catalysts include tris(dibenzylideneacetone)dipalladium (O), bis(dibenzylideneacetone)palladium (O) and palladium acetate. Preferred ligands include 2,2'-bis(diphenylphosphino-1,1'-binaphthyl, bis(2-diphenylphosphinophenyl)ether and 1,1'-bis(diphenylphosphino)ferrocene. Preferred bases include sodium methoxide and sodium isopropoxide. The resulting benzophenone imines are cleaved to the free amines, e.g. by treatment with dilute acid, such as 2N hydrochloric acid.

The other steps are carried out as described herein.

In starting compounds and intermediates which are converted to the compounds of the invention in a manner described herein, functional groups present, such as amino, carboxyl, and hydroxy groups, are optionally protected by conventional protecting groups that are common in preparative organic chemistry. Protected amino, carboxyl, and hydroxy groups are those that can be converted under mild conditions into free amino, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", third edition, Wiley, New York, 1999.

In the processes cited herein, reactive functional derivatives of carboxylic acids represent, for example, anhydrides (especially mixed anhydrides), acid halides, acid azides, lower alkyl esters, and activated esters thereof. Mixed anhydrides are preferably such from pivalic acid, or a lower alkyl (ethyl, isobutyl) hemiester of carbonic acid; acid halides are for example chlorides or bromides; activated esters for example succinimido, phthalimido or 4-nitrophenyl esters; lower alkyl esters are for example the methyl or ethyl esters.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization, or resolved by enzymatic resolution.

Any resulting racemates of intermediates can be resolved into the optical antipodes by known methods, e.g., by separation of the diastereoisomeric salts thereof, obtained with an optically active acid or base, and liberating the optically active acidic or basic compound. The amine intermediates can thus be resolved into their optical antipodes e.g., by fractional crystallization of salts of d- or l-carboxylic acids (e.g., d- or l-tartaric acid or d- or l-camphorsulfonic acid). Racemic products can also be resolved by chiral chromatography, e.g., high-pressure liquid chromatography using a chiral absorbent.

Finally, compounds of the invention are either obtained in the free form, or as a salt thereof if salt forming groups are present.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$)-alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit microsomal triglyceride transfer protein (MTP) and apolipoprotein B (apo B) secretion, and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g., to the skin and eyes, are preferably aqueous solutions, ointments, creams or gels well known in the art.

The pharmaceutical formulations contain an inhibiting amount of a compound of the invention as defined above, either alone or in combination with another therapeutic agent, e.g., each at an effective therapeutic dose as reported in the art. Such therapeutic agents are well known in the art.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 1 and 1000 mg, advantageously between about 10 and 500 mg of the active ingredient, preferably between about 10 and 100 mg.

The present invention also relates to methods of using the compounds of the invention and their pharmaceutically acceptable salts, or pharmaceutical compositions thereof, in mammals for the treatment of elevated levels of MTP and of apo B and conditions related thereto.

The compounds of the invention are inhibitors of microsomal triglyceride transfer protein (MTP) and of apolipoprotein B (apo B) secretion and are thus useful for lowering serum lipid levels, including serum triglyceride and serum cholesterol levels. Such compounds are therefore useful for the treatment and prevention of hyperlipedemia, hypercholesterolemia and hypertriglyceridemia and diseases associated therewith, e.g., cardiovascular diseases including cardiac ischemia, atherosclerosis and its clinical sequelae, as well as obesity, pancreatitis and diabetes.

The above-cited properties can be demonstrated in vitro and in vivo tests using the methods as described in WO 00/05201, especially as described in the corresponding disclosure from page 20, last paragraph, up to page 25, last paragraph. The corresponding relevant subject matter of said PCT application is herewith incorporated by reference into the present specification.

Illustrative of the invention, the compound of Example 14 demonstrates an IC50 of about 2 nM in the apo B assay and an $IC_{50}$ of about 40 nM in the MTP assay.

Illustrative of the invention, the compound of example 14 lowers both plasma triglycerides and cholesterol at a dose of 5 mg/kg. p.o.

Accordingly, the present invention relates to a method of inhibiting microsomal triglyceride transfer protein; decreasing apolipoprotein B secretion and treating microsomal triglyceride transfer protein or apolipoprotein B dependent conditions in mammals which comprises administering to a mammal in need thereof an effective amount of a compound of the present invention.

Likewise, the present invention relates to the use of a compound according to the present invention for the manufacture of a medicament for inhibiting microsomal triglyceride transfer protein; decreasing apolipoprotein B secretion and treating microsomal triglyceride transfer protein or apolipoprotein B dependent conditions and related conditions and diseases.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g., microanalysis and spectroscopic characteristics (e.g., MS, IR, NMR). Abbreviations used are those conventional in the art. The concentration for $[\alpha]_D$ determinations is expressed in mg/mL. Compounds are purified by standard methods, e.g., recrystallization or flash chromatography.

EXAMPLES

A. Preparation of 6-methyl-4'-trifluoromethyl-1,1'-biphenyl-2-carboxylic acid A solution of 2-bromo-3-methylbenzoic acid (21.5 g, 100 mmol) in 500 mL of methanol and 8 mL of concentrated sulfuric acid is refluxed overnight. Methanol is removed under reduced pressure, the residue is taken up in ether, washed with sodium bicarbonate, brine, and dried over magnesium sulfate, filtered, and evaporated under reduced pressure to give methyl 2-bromo-3-methylbenzoate as an oil.

A mixture of methyl 2-bromo-3-methylbenzoate (22.33 g, 97.5 mmol), potassium phosphate (82.8 g, 390 mmol), [1,1'-bis(diphenylphosphino)-ferrocene]dichloro palladium (II) complex with dichloromethane (1:1) (3.98 g, 4.87 mmol), and p-trifluoromethylphenylboronic acid (22.2 g, 117 mmol) in 500 mL of DME is degassed and refluxed under an atmosphere of argon overnight. The mixture is concentrated, poured into water and extracted with ethyl acetate. The combined organic extracts are washed with brine, dried over magnesium sulphate, filtered and evaporated under reduced pressure. The residue is purified by silica gel chromatography eluting with ethyl acetate/toluene (1:9) to give methyl 6-methyl-4'-trifluoromethyl-1,1'-biphenyl-2-carboxylate.

Alternatively, methyl 6-methyl-4'-trifluoromethyl-1,1'-biphenyl-2-carboxylate can be prepared as follows:

To a slurry of 3-methylsalicylic acid (200 g) in 600 mL of methanol at −15° is added 65.7 g of concentrated sulfuric acid. The mixture is treated at reflux temperature for 5 days. The reaction mixture is concentrated, and methyl-t-butyl ether (500 mL) and water (250 mL) are added. The ether layer is separated, washed with bicarbonate solution and evaporated to dryness to give methyl 3-methylsalicylate an oil.

A mixture of methyl 3-methylsalicylate (150 g), pyridine (178.5 g) and methylene chloride (1500 mL) is cooled to −5°. Triflic anhydride (305.6 g) is added over 30 minutes. 4-Dimethylaminopyridine (3.31 g) is then added, the reaction mixture is stirred at room temperature overnight, washed with 1N HCl, then with saturated sodium bicarbonate solution and finally with brine. The solution is dried over magnesium sulfate, and evaporated to dryness in the presence of toluene. The residual oil is dissolved in toluene to obtain a volume of 3000 mL and the solution of methyl 2-trifluoromethanesulfonyloxy-3-methylbenzoate is used as is in the next step.

A solution of p-trifluoromethylbromobenzene (814.8 g) and triisopropoxyborane (681.0 g) in tetrahydrofuran (6300 mL) is cooled to −78° and n-butyllithium (2.5 m in hexanes, 1448 mL) is added over 30 minutes at a temperature below −60° to yield p-trifluoromethylphenylboronic acid.

To a solution of methyl 2-trifluoromethanesulfonyloxy-3-methylbenzoate (900 g, in toluene), potassium carbonate (629.6 g), tetrahydrofuran (2700 mL) and deionized water (5400 mL) under nitrogen is added tetrakis (triphenylphosphine)palladium (0) (104.6 g). To this is added the above solution of p-trifluoromethylphenylboronic acid and the mixture is heated at reflux for 2 days. The reaction mixture is filtered and evaporated to dryness. The residue is partitioned between water and ethyl acetate. The ethyl acetate layer is separated and evaporated to dryness. The residue is taken up in heptane-ethyl acetate (9:1), the mixture is filtered and the filtrate is evaporated to dryness to give methyl 6-methyl-4'-trifluoromethylbiphenyl-2-carboxylate as an oil.

A mixture of methyl 6-methyl-4'-trifluoromethyl-1,1'-biphenyl-2-carboxylate (13.6 g, 46.3 mmol), and 1N NaOH (92.5 mL, 92.5 mmol) in 225 mL of ethanol is refluxed for 5 h. Water is added to the mixture and the aqueous layer is washed with ether. The aqueous layer is acidified with 1N HCl and extracted with ethyl acetate, dried over magnesium sulfate, filtered, and concentrated under reduced pressure. The product is purified by crystallization from ethyl acetate/hexanes to yield 6-methyl-4'-trifluoromethyl-1,1'-biphenyl-2-carboxylic acid melting at 202–203° C. $^1$HNMR CDCl$_3$: 300 MHz): δ 7.87 (1H, d), 7.65 (2H, d), 7.47 (1H, d), 7.35 (1H, t), 7.25 (2H, d), 2.05 (3H, s). MS m/z 279 (M−1).

Alternately, 6-methyl-4'-trifluoromethyl-1,1'-biphenyl-2-carboxylic acid can be prepared as follows:

3-Methylsalicylic acid is esterified to methyl 3-methylsalicylate by reaction under reflux for about 48 hours with methanol in the presence of trimethyl orthoformate (4.0 moles) and concentrated sulfuric acid (1.1 moles) while removing by distillation the generated methyl formate and replacing the methanol which is lost by distillation. The reaction mixture is then evaporated to dryness at 40° under vacuum and toluene is added. The toluene solution is washed with water, then 20% aqueous potassium bicarbonate solution and saturated sodium chloride solution. The toluene solution is filtered through neutral activated aluminum oxide and evaporated to dryness to yield methyl 3-methylsalicylate as a liquid.

To a solution of 1.0 mole of methyl 3-methylsalicylate in toluene are added 2.33 moles of 4-methylmorpholine and 0.022 moles of 4-dimethylaminopyridine. The resulting solution is then treated with 1.07 moles of trifluoromethanesulfonic acid anhydride (triflic anhydride) at −15° C. The reaction mixture is stirred overnight at −3 to −4° C. and washed consecutively with 3.7% aqueous HCl, 20% potassium bicarbonate solution and saturated sodium chloride solution. The toluene solution is then filtered through alumina and evaporated to dryness at less than 50° C. and about 40 mmHg pressure. The residue is distilled at 50° C. and 5 mmHg pressure to obtain methyl 3-methyl-2-trifluoromethanesulfonyloxybenzoate as an oil.

A solution of 140.75 g of 4-bromobenzotrifluoride and 117.6 g of triisopropylborate in 1050 mL of dry and peroxide-free THF is cooled to −72±3° C. 275 mL of 2.5 M n-BuLi solution in hexane are slowly added over a period of 90 minutes at such a rate that the internal temperature of the reaction mixture remains below −60° C. The mixture is stirred at −65 to −70° C. for 30 minutes after the addition and warmed to 0° C. over 90 minutes. This solution of diisopropyl 4-trifluoromethylphenylboronate is used as is in the next step.

A solution of 155 g of methyl 3-methyl-2-trifluoromethylmethanesulfonyloxybenzoate, 107.8 g of potassium carbonate in 467.5 mL of THF and 935 g of deionized water is stirred under nitrogen for 20 minutes. 15.0 g of Tetrakis(triphenylphosphine)palladium (0) and ~1610 mL of boronate solution from step above are added and the reaction mixture is heated under gentle reflux (~64° C.) for 16 hours. The reaction mixture is cooled to room temperature and filtered through a pad of 40 g of the filter agent Celite® 521. The filter cake is washed with 100 mL of THF and the total filtrate is partially evaporated under reduced pressure (110–120 mbar/40° C.) to remove about 1500 mL of distillate and obtain a three phase mixture (about 1250 mL). 500 mL of t-Butyl methyl ether and 200 mL of 2% sodium chloride solution are added. The mixture is stirred for 5 minutes and filtered through a pad of 40 g of Filter agent, Celite® 521 and the filter cake is washed with 100 mL of t-butyl methyl ether. The top organic layer (1100 mL) is separated from the bottom aqueous layer (950 mL). The bottom aqueous layer (950 mL) is extracted with 300 mL of t-butyl methyl ether. The combined upper organic phases are washed with 300 mL of 2% sodium chloride solution and evaporated under reduced pressure (28 mbar/40° C.) to obtain methyl 6-methyl-4'-trifluoromethyl-biphenyl-2-carboxylate.

6N Sodium hydroxide (260 mL) is added slowly at room temperature to a solution of 183 g of methyl 6-methyl-4'-trifluoromethyl-biphenyl-2-carboxylate in 1200 mL of methanol. The reaction mixture is heated under gentle reflux for 2.5 hours, cooled to room temperature and diluted with 300 mL of water. The reaction mixture is evaporated under reduced pressure (110–120 mbar/40° C.) to a suspension of about 750 mL which is filtered through the filter agent Celite® 521, and the filter cake is washed sequentially with 250 mL of water and 250 mL of heptane. The organic layer is separated and the aqueous layer is washed with 250 mL of heptane. The aqueous layer is acidified with 500 mL of 4N hydrochloric acid and extracted with ethyl acetate. The ethyl acetate extract is washed with water and filtered through the filter agent Celite® 521. The ethyl acetate solution (ca. 1000 mL) is evaporated under reduced pressure. (110–120 mbar/40° C.) to a volume of 600 mL to which is added heptane (3125 mL). The suspension is then heated to reflux until a clear solution is obtained, the solution is cooled to 0° C. and the resulting solid is filtered off to yield 6-methyl-4'-trifluoromethyl-1,1'-biphenyl-2-carboxylic acid.

B. Preparation of (5-aminoindan-2-yl)-carbamic acid tert-butyl ester

To N-(5-nitro-indan-2-yl)-acetamide (23.5 g, 107 mmol) is added 2N hydrochloric acid (500 mL). The mixture is heated to reflux for 24 h and then concentrated in vacuo. Methanol (100 mL) is added to the residue and the mixture is concentrated in vacuo. Toluene (100 mL) is added and the mixture is again concentrated. A solution of the residue in methanol (100 mL) is warmed, diethyl ether (500 mL) is added and the mixture is let stand overnight. The solid is collected by filtration and air dried to yield 2-amino-5-nitroindane hydrochloride as a white solid.

To a solution 2-amino-5-nitro-indane hydrochloride (20.4 g, 95 mmol) in methylene chloride (500 mL) under nitrogen is added diisopropylethyl amine (14.7 g, 114 mmol). To this is added a solution of di-tert-butyldicarbonate (22.8 g, 105 mmol) in methylene chloride. The mixture is stirred for 16 h, washed with brine, 1N hydrochloric acid, brine, and then dried over sodium sulfate. The solution is concentrated in vacuo to give a solid residue which is triturated with diethyl ether to give (5-nitro-indan-2-yl)-carbamic acid tert-butyl ester as a white solid.

A solution of (5-nitro-indan-2-yl)-carbamic acid tert-butyl ester (3.52 g, 12.6 mmol) in ethanol (100 mL) is degassed and 10% palladium on carbon added. The reaction is evacuated and placed under 1 atm $H_2(g)$ for 2 h. Filtration of the reaction mixture through Celite is followed by concentration of the filtrate under reduced pressure to give (5-amino-indan-2-yl)-carbamic acid tert-butyl ester as an oil which is used directly without further purification.

C. Preparation of optically active 5-aminoindan-2-yl-carbamic acid methyl ester (a) The alcohol, (1-hydroxy-indan-2-yl)-carbamic acid methyl ester (1S-trans) prepared from L-phenylalanine (18.7 g, 0.09 mol) (J. Org. Chem. 1983, 48, 2675–2679) is suspended in methylene chloride and cooled to 0° C. Pyridine (10.7 g, 0.135 mol) is added followed by acetyl chloride (10.5 g, 0.135 mol). The mixture is stirred for 1 h, and then washed with sodium bicarbonate, 1N HCl and saturated sodium chloride. The organic layer is dried over $Na_2SO_4$, filtered and evaporated under reduced pressure to give (1-acetyloxy-indan-2-yl)-carbamic acid methyl ester (1S-trans).

To 90% $HNO_3$ (55.1 mL, 0.8 mol) under nitrogen at −30° C. is added 100 mL of trifluoroacetic acid followed by the addition of trifluoroacetic anhydride (100 g, 0.476 mol) over 5 minutes. The above carbamate (1-acetyloxy-indan-2-yl)-carbamic acid methyl ester (1S-trans)) (20.0 g, 0.08 mol) in 34 mL of methylene chloride is added slowly (over 90 min.) keeping the temperature between −30 and −35° C. The reaction is worked up by adding 100 mL of water and warmed to 0° C. to give two layers. The layers are separated and the aqueous layer extracted with methylene chloride. The combined organic extracts are washed with 100 mL of water (pH is adjusted to 8.5 with sodium bicarbonate), and with cold water. The organic layer is dried over $MgSO_4$, filtered and evaporated to give crude product. The crude product is crystallized from ethyl acetate and further precipitated by the addition of heptane to give (1-acetyloxy-6-nitro-indan-2-yl)-carbamic acid methyl ester (1S-trans); mp 164–167° C.

The above ester (16.5 g, 0.056 mol) is suspended in 275 mL of methanol at room temperature. 1N Sodium hydroxide solution (112 mL, 0.112 mol) is added and the mixture is stirred at room temperature for 15 minutes. The reaction is diluted with water and the solid is collected. The solid is reslurried in 250 mL of ice-water and pH is adjusted to 6.5–7.0 with 1N HCl. The solution is filtered and washed with water, and the product is collected and dried under vacuum to give (1-hydroxy-6-nitro-indan-2-yl)-carbamic acid methyl ester (1S-trans); mp 201–203° C.

The above nitro alcohol (6.0 g, 0.023 mol) is dissolved in 300 mL of acetic acid containing 3 mL of water at 50° C. The mixture is cooled to room temperature and $HClO_4$ (6 g, 0.042 mol) and 10% Pd/C (6 g) are added and the mixture is hydrogenated at 50 psi for two days. Fresh catalyst (3 g) is added twice during the reaction period. The reaction mixture is filtered through celite, the filtrate is concentrated and the residue is washed with ice-water, dried over MgSO$_4$. The solution is filtered and solvent removed under reduced pressure to give (S)-(5-amino-indan-2-yl)-carbamic acid methyl ester; mp 140–142° C.

(R)-(5-aminoindan-2-yl)-carbamic acid methyl ester, m.p. 144–145° C., is similarly prepared from (1-acetyloxyindan-2-yl)-carbamic acid methyl ester (1R-trans), starting with D-phenylalanine instead of L-phenylalanine.

(b) Alternately, (R)-(5-aminoindan-2-yl)-carbamic acid methyl ester is prepared as follows:

A mixture of ninhydrin (33 g, 0.185 mol) and acetic acid (554 g) is stirred at room temperature (rt) under N$_2$ until complete dissolution of ninhydrin. Sulfuric acid is then added (54.42 g, 0.555 mol) followed by hydroxylamine sulfate (31.63 g, 0.193 mol). The mixture is heated to 55° C. for 30 minutes and is then allowed to cool to room temperature. 10% Pd/C (2.64 g, 8% w/w) is added to the resulting yellow suspension and the mixture is hydrogenated at a pressure of H$_2$ of 20 psi. After stirring for 1 hour at rt, the H$_2$ pressure is increased to 40 psi and the temperature increased to 35° C. After stirring for 8 hours, the reaction is allowed to cool before filtration on a pad of Celite (20 g). The Celite cake is washed with acetic acid (70 g). The filtrate is concentrated, xylene (250 g) is added to the resulting slurry and the mixture concentrated again. Xylene (170 g) is added followed by slow addition of 20% NaOH (367 g) until a basic pH and a clear separation of the organic and aqueous layers is obtained. The xylene layer is then separated and filtered. The HCl salt is then precipitated out by slow addition of a 4 N HCl solution in 1-pentanol (51 g). The suspension is cooled to 0° C. and filtered. The cake is rinsed with heptane (100 g) and dried under vacuum to yield 2-amninoindane hydrochloride as a white powder.

A solution of 118.8 g of 2-aminoindane hydrochloride in 594 mL of water is heated to a temperature of 58–60° C. and 120.0 g of bromine is added over a period of 50 minutes while maintaining an internal temperature at 58 to 62° C. The mixture is stirred at 60–62° C. for 1 hour and 107 mL of hydrobromic (48%) is added over a period of 5 minutes while maintaining the internal temperature of 60–62° C. The mixture is stirred for an additional 10 minutes. The reaction mixture is cooled to an internal temperature of 20–23° C. over a period of 1 hour. The resulting solid is collected by filtration, washed with 3×133 mL of 2-propanol and dried at 58–60° C. under vacuum (10–30 torr) to obtain crude (±)-5-bromo-2-aminoindan hydrobromide. A suspension of 156.0 g of crude (±)-5-bromo-2-aminoindane hydrobromide in 390 mL of deionized water is heated to a temperature at 95–100° C. to obtain a clear solution. The solution is cooled to an internal temperature at 20–23° C. over a period of 2.5 hours and stirred at 20–23° C. for an additional 30 minutes. The resulting solid is collected by filtration and washed with 3×20 mL of water (precooled to 0–5° C.), and dried at 60–65° C. under vacuum (10–30 torr) with nitrogen bleeding to obtain (±)-5-bromo-2-aminoindane hydrobromide. A mixture of 130.0 g of (±)-5-bromo-2-aminoindane hydrobromide and 1500 mL of isopropyl acetate is stirred at 20–25° C. under nitrogen. A solution (precooled to 20–25° C.) of 26.62 g of sodium hydroxide and 186.35 g of sodium chloride in 750 mL of water is added over a period of 5 minutes while maintaining an internal temperature at 20–25° C. The suspension is stirred efficiently until all the solid dissolves (30 minutes). The organic layer is separated and the aqueous layer is extracted with 750 mL of isopropyl acetate. The organic layers are combined to afford ~2330 mL of a solution of (±)-5-bromo-2-aminoindane free base.

To the above solution is added 1300 mL of isopropyl acetate and 930 mL of methanol. The solution is stirred under nitrogen and heated to an internal temperature of 65° C. to achieve a gentle refluxing, over a period of 15 minutes. A solution of 103.1 g of (1S)-(+)-10-camphorsulfonic acid in 660 mL of methanol is added over a period of 15 minutes while maintaining an internal temperature of 60–65° C. to obtain a clear solution followed by 185 mL of methanol to achieve a v/v ratio of isopropyl acetate:methanol of about 2:1. The reaction mixture is cooled to 20–23° C. over a period of 2 hours. The mixture is stirred at room temperature (20–23° C.) for an additional 2 hours. The solid is collected, washed with 500 mL of precooled (to 0–2° C.) mixture of isopropyl acetate and methanol (2:1; v/v) in two equal portions of 250 mL each, and dried at 50–55° C. (100 mm Hg) to obtain crude (R)-5-bromo-2-aminoindane (1S)-(+)-10-camphorsulfonate salt as a white solid. A mixture of 90.0 g of crude (R)-5-bromo-2-aminoindane (1S)-(+)-10-camphorsulfonate salt and 900 mL of methanol is heated to a temperature of 65° C. to achieve a gentle refluxing. This suspension is stirred at 65° C. for 1 hour and the reaction mixture is cooled to 20–23° C. over a period of 2 hours and stirred at 20–23° C. for an additional 2 hours. The resulting solid is collected, washed with 190 mL of precooled (to 0–2° C.) mixture of isopropyl acetate and methanol (1:1; v/v) in two equal portions of 95 mL each. The solid is dried at 50–55° C. (100 mm Hg) to obtain (R)-5-bromo-2-aminoindane (1S)-(+)-10-camphosulfonate salt as a white solid (98.7% optical purity).

A suspension of 111.1 g of (R)-5-bromo-2-aminoindane (1S)-(+)-10-camphorsulfonate salt and 300 mL of isopropyl acetate is stirred at 20–25° C. and a solution of 15.0 g of sodium hydroxide and 75.0 g of sodium chloride in 300 mL of water is added over a period of 10 minutes while maintaining an internal temperature at 20 to 25° C. The suspension is stirred for 30 minutes or until all the solids dissolve. The organic layer is separated and the aqueous layer is extracted with 100 mL of isopropyl acetate. The organic layers containing (R)-5-bromo-2-aminoindane free base are combined. A solution of 60 g of sodium bicarbonate in 600 mL of water is added and the resulting white slurry is stirred under nitrogen and cooled to a temperature of 0–5° C. over a period of 15 minutes. A solution of 35.4 g of methyl chloroformate in 200 mL of isopropyl acetate is added over a period of 45 minutes while maintaining an internal temperature of 0–5° C. and the mixture is stirred at this temperature for an additional 1 hour. The organic layer is separated and washed with 150 mL of 1 N sulfuric acid is added, then with a solution of 10 g of sodium bicarbonate in 100 mL of deionized water and finally with 150 mL of deionized water. The organic layer is concentrated under vacuum (100–300 torr) at a temperature of 40–50° C. to ~150 mL of a slurry. Heptane (500 mL) is added and the mixture is again concentrated under vacuum (100–200 torr) at a temperature of 40–50° C. to about 300 mL of a slurry. Heptane (500 mL) is again added and the mixture is cooled to an internal temperature of 0–5° C. The solid is collected and washed with 40 mL of heptane in two equal portions of 20 mL each. The solid is dried at 60–65° C. under vacuum (10–30 torr) to obtain (R)-(5-bromoindan 2-yl)-carbamic acid methyl ester as a crystalline white solid.

A mixture of 94.55 g of (R)-(5-bromo-indan-2-yl)-carbamic acid methyl ester, 69.78 g of benzophenone imine, 2.32 g of (±)-2,2'-bis(diphenylphosphino)-1,1'-binaphthyl, 26.47 g of sodium methoxide, and 1.60 g of tris (dibenzylideneacetone)dipaladium(0) in 875 mL of deoxygenated and dry toluene is stirred under nitrogen and heated to an internal temperature of 70–75° C. over a period of 15 minutes. The mixture is stirred at this temperature for 16 hours, and cooled to 30–35° C. over a period of 30 minutes. Isopropyl acetate (875 mL) is added over a period of about 15 minutes and the mixture is further cooled to 20–25° C. Water (875 mL) is added over a period of about 15 minutes and the suspension is stirred for an additional 10 minutes. The solid is collected and washed with 175 mL of toluene followed by 263 mL of water to obtain crude (R)-[5-(diphenylmethylene)amino-indan-2-yl]-carbamic acid methyl ester as a yellow solid. The reaction flask, Buchner funnel, and filtration flask are washed with about 400 mL of isopropyl acetate and this is combined with the filtrate. The organic layer is separated and washed with a solution of 43.75 g of citric acid in 831 mL of water to afford a solution of additional crude (R)-[5-(diphenylmethylene)amino-indan-2-yl]-carbamic acid methyl ester which is added to the above crude product. 2 N Hydrochloric acid (170 mL) is added and the mixture is stirred at an internal temperature of 20–25° C. for 16 hours. Water (350 mL) is then added and the biphasic solution is stirred for an additional 10 minutes. The mixture is filtered, the aqueous layer is separated and washed with a total of 1750 mL of isopropyl acetate in two equal portions to yield about 2200 mL of a solution of (R)-(5-amino-indan-2-yl)-carbamic acid methyl ester hydrochloride. The solution is cooled to 0–5° C. over a period of 15 minutes. 2 N sodium hydroxide (2175 mL) is added to adjust the pH to 8–9 in 45 minutes while maintaining an internal temperature below 18° C. A solution of 93.5 g of sodium chloride in 267 mL of water is added and the resulting suspension is stirred at this temperature for an additional 30 minutes. The solid is collected by filtration and washed with 438 mL of water in two equal portions. The solid is dried at 55–60° C. under vacuum (10–30 torr) with nitrogen bleeding to obtain crude (R)-(5-amino-indan-2-yl)-carbamic acid methyl ester as a solid.

A mixture of crude (R)-(5-amino-indan-2-yl)-carbamic acid methyl ester, activated carbon (about 0.15 times weight of the weight of crude material) and methanol (about 20 times volume of the weight of crude material) is stirred and heated to an internal temperature at 65° C. to achieve a gentle refluxing over a period of 15 minutes. The mixture is stirred at this temperature for an additional 2 hours and filtered through celite to afford a solution of (R)-(5-aminoindan-2-yl)-carbamic acid methyl ester. The solution is concentrated under vacuum (200–400 torr) at an internal temperature of 45–55° C. to a small volume. Water is added (the ratio of methanol and water should be about 1:1). The mixture is cooled to an internal temperature of 0–5° C. The resulting suspension is filtered, the solid is washed with a precooled mixture of methanol and water (1:1; v/v) and dried at 55–60° C. under vacuum (10–30 torr) under nitrogen to yield (R)-(5-amino-indan-2-yl)-carbamic acid methyl ester.

D. Preparation of N-(2-aminoindan-5-yl)-6-methyl-4'-trifluoromethyl-1,1'-biphenyl-2-carboxamide A solution of (5-nitro-indan-2-yl)-carbamic acid tert-butyl.ester (3.52 g, 12.6 mmol) in ethanol (100 mL) is degassed and 10% palladium on carbon added. The reaction is evacuated and placed under 1 atm H$_2$(g) for 2 h. Filtration of the reaction mixture through Celite is followed by concentration of the filtrate under reduced pressure to give (5-amino-indan-2-yl)-carbamic acid tert-butyl ester as an oil which is used directly without further purification.

To a solution of (5-amino-indan-2-yl)-carbamic acid tert-butyl ester (12.5 mmol) in methylene chloride (75 mL) is added diisopropylethyl amine (3.3 g, 25 mmol) followed by a solution of 6-methyl-4'-trifluoromethyl-1,1'-biphenyl-2-carboxylic acid chloride (12.6 mmol) in methylene chloride. After stirring 16 h, the reaction mixture is poured into ethyl acetate and washed with 1N HCl, NaHCO$_3$ solution, and brine. The organic layer is dried (MgSO$_4$) and concentrated under reduced pressure to give a solid. Recrystallization from toluene gives {5-[(6-methyl-4'-trifluoromethyl-1,1'-biphenyl-2-carbonyl)-amino]-indan-2-yl}-carbamic acid tert-butyl ester.

A solution of {5-[(6-methyl-4'-trifluoromethyl-1,1'-biphenyl-2-carbonyl)-amino]-indan-2-yl}-carbamic acid tert-butyl ester (5.19 g, 10.5 mmol) in formic acid (40 mL) is heated to 40° C. with stirring. After 3 h, the reaction mixture is cooled to room temperature and stirring is continued for 16 h. The reaction mixture is concentrated under reduced pressure and the resulting oil dissolved in ethyl acetate. The organic layer is washed with 8% NaHCO$_3$ solution until the aqueous layer remains basic at which point a precipitate forms in the organic layer. The precipitate is collected by filtration to give N-(2-aminoindan-5-yl)-6-methyl-4'-trifluoromethyl-1,1'-biphenyl-2-carboxamide.

E. Preparation of (R)-N-(2-aminoindan-5-yl)-6-methyl-4'-trifluoromethyl-1,1'-biphenyl-2-carboxamide To an ice bath cooled suspension of 6-methyl-4'-trifluoromethyl-1,1'-biphenyl-2-carboxylic acid (17.7 g, 63.2 mmol) in 500 mL of methylene chloride is added oxalyl chloride (22.1 mL, 253 mmol) followed by 4 drops of DMF. The reaction is stirred for 2 h and another 22 mL of oxalyl chloride and 4 drops of DMF is added. Stirring is continued another 2 h. The mixture is concentrated under reduced pressure to yield the acid chloride. Methylene chloride (100 mL) is added and the acid chloride is used as is in subsequent reactions.

To an ice bath cooled solution of (R)-(5-aminoindan-2-yl)-carbamic acid methyl ester (9.5 g, 46.1 mmol), ([α]$_D$=−26.29° (c=9.87 mg/mL, DMSO); mp 144–145° C.) and pyridine (4.48 mL, 55.5 mmol) in 200 mL of methylene chloride is added 6-methyl-4'-trifluoromethyl-1,1'-biphenyl-2-carboxylic acid chloride (80.5 mL of a 0.63 M solution in methylene chloride, 50.7 mmol). The reaction is stirred for 15 minutes at room temperature. The mixture is washed with 1N HCl, bicarbonate and brine. The organic layer is dried over magnesium sulfate, filtered, and concentrated under reduced pressure. The product is purified by crystallization from ethyl acetate/hexanes (1:2) to give (R)-6-methyl-4'-trifluoromethyl-1,1'-biphenyl-2-carboxylic acid (2-methoxycarbonylaminoindan-5-yl)-amide as crystalline solid, mp 112–114° C. [α]$_D$=−12.85°, c=11.36 mg/mL DMSO.

(R)-6-methyl-4'-trifluoromethyl-1,1'-biphenyl-2-carboxylic acid (2-methoxycarbonylaminoindan-5-yl)-amide (6.5 g, 13.9 mmol) is dissolved in acetonitrile (325 mL) and cooled to 0° C. under nitrogen. Iodotrimethylsilane (11.1 g, 55.6 mmol) is added dropwise, the mixture is allowed to warm to room temperature and is stirred overnight. Methanol (100 mL) is added and the mixture is stirred for 1 hour and then concentrated in vacuo. The residue is dissolved in ethyl acetate (750 mL) and washed with saturated sodium bicarbonate (2×125 mL), water (125 mL), 5% Na$_2$S$_2$O$_3$ solution (125 mL), water (125 mL), and brine (50 mL). The organic phase is dried over sodium sulfate and concentrated to afford (R)-N-(2-aminoindan-5-yl)-6-methyl-4'-trifluoromethyl-1,1'-biphenyl-2-carboxamide.

F. Preparation of 2-(4-trifluoromethyl-phenyl)-nicotinic acid chloride

To a solution of 2-chloronicotinic acid (2.00 g, 12.69 mmol) in DMF (40 mL) at 0° C. is added cesium carbonate (4.96 g, 15.23 mmol) followed by iodomethane (0.95 mL, 15.23 mmol). The reaction mixture is warmed to room temperature and stirred 16 h. Dilution with ethyl acetate is followed by washing with water, 8% NaHCO$_3$ solution and brine. The organic layer is dried (MgSO4$_4$) and concentrated under reduced pressure to give 2-chloronicotinic acid methyl ester as an oil: $^1$H NMR (CDCl$_3$, 300 MHz): δ 8.55 (1H, dd), 8.18 (1H, dd), 7.33 (1H, dd), 3.97 (3H, s).

2-(4-Trifluoromethyl-phenyl)-nicotinic acid methyl ester is prepared by palladium [PdCl$_2$ (dppf)] catalyzed coupling of 2-chloronicotinic acid methyl ester (1.45 g, 8.45 mmol) and 4-trifluoromethylbenzeneboronic acid (2.41 g, 12.68 mmol) to give an oil: $^1$H NMR (CDCl$_3$, 300 MHz): δ 8.80 (1H dd), 8.19 (1H, dd), 7.67 (4H, q), 7.40 (1H, dd), 3.70 (3H, s).

MS (ES+) m/z 282 (M+1).

To a solution of 2-(4-trifluoromethyl-phenyl)-nicotinic acid methyl ester (0.626 g, 2.228 mmol) in 1:1 THF:H$_2$O (10 mL) is added LiOH.H$_2$O (0.187 g, 4.456 mmol). After 3.5 h, the reaction mixture is concentrated to dryness under reduced pressure. To a slurry of the crude lithium salt in methylene chloride (10 mL) is added oxalyl chloride (0.78 mL, 8.91 mmol) followed by a few drops DMF. After stirring 16 h, the reaction mixture is concentrated to dryness under reduced pressure to give the acid chloride which is used as is without purification.

G. Preparation of 2-(4-trifluoromethylbenzyloxy)-3-methylbenzoic acid

To a solution of 2-hydroxy-3-methylbenzoic acid (18.1 g, 119 mmol) in 70 mL of methanol is added dropwise 3.3 mL of concentrated sulfuric acid. The resulting solution is heated under reflux for 24 hours. Another 7 mL of concentrated sulfuric acid is added and the reaction is heated at 70° C. overnight. The mixture is cooled and a pink layer separated. This layer is dissolved in 200 mL of ethyl acetate and the solution is washed with saturated aqueous sodium bicarbonate and brine, dried over sodium sulfate, filtered and concentrated to give an oil which is purified by chromatography on silica gel using a mixture of 30% ethyl acetate and 70% hexane as the eluent. Methyl 2-hydroxy-3-methylbenzoate is obtained as a clear oil.

Sodium hydride is added to a solution of methyl 2-hydroxy-3-methylbenzoate (694 mg, 4.18 mmol) in 15 mL of DMF at 0° C. The reaction is stirred for 15 minutes after which 4-trifluoromethyl-benzyl bromide (1.0 g, 4.18 mmol) is added. The reaction is allowed to warm up to room temperature and stirred overnight. The mixture is partitioned between ethyl acetate and water. The organic phase is washed with brine, dried over sodium sulfate, filtered and concentrated. The residue is chromatographed on silica gel using 4% ethyl acetate in hexane as the eluent to obtain methyl 2-(4-trifluoromethylbenzyloxy)-3-methylbenzoate as a clear liquid.

To a solution of methyl 2-(4-trifluoromethylbenzyloxy)-3-methylbenzoate (1.17 g, 3.61 mmol) is added 10 mL of 1N LiOH. The mixture is stirred at room temperature for 3 days, then concentrated under vacuum. The residue is washed with hexane, then acidified to pH 1 with 6N HCl. A white precipitate forms which is extracted with ethyl acetate. The organic solution is dried over sodium sulfate, filtered and concentrated to give the title acid as a white solid, m.p. 104–106° C.

EXAMPLE 1

6-Methyl-4'-trifluoromethyl-1,1'-biphenyl-N-[2[4-(methoxycarbonyl)-piperazino]-indan-5-yl]-2-carboxamide

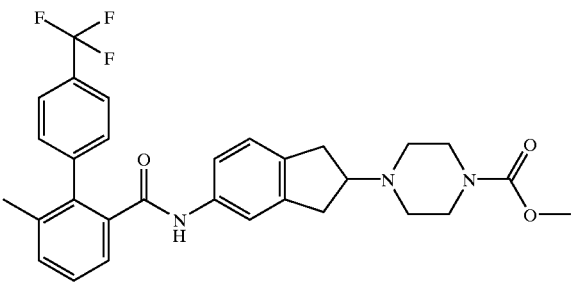

Step A. To 2-indanol (13.4 g, 100 mmol) in 100 mL of methylene chloride at 0° C. are added pyridine (8 mL), acetyl chloride (7.11 mL, 100 mmol) and dimethylaminopyridine (1.22 g, 10 mmol). After 1 hour an additional 4 mL of pyridine and 3.5 mL of acetyl chloride are added. The mixture is stirred for 1 hour and quenched with sodium bicarbonate. The organics are washed with 1N HCl, brine, and dried over sodium sulfate. The mixture is filtered and concentrated to give 2-acetoxyindane as a solid.

Step B. To a 0° C. solution of 2-acetoxyindane from Step A (17.6 g, 100 mmol) in 35 mL of trifluoroacetic acid (TFA) is added fuming nitric acid (25.5 mL, 625 mmol) dropwise. The solution is stirred for 4 hours, then concentrated in vacuo and poured into water. The mixture is extracted with methylene chloride and the extract is washed with sodium bicarbonate and brine, filtered and concentrated. The residue is slurried with ether. The product is collected and dried to give 2-acetoxy-5-nitroindane as a light yellow solid.

Step C. A solution of nitro compound from Step B (10 g, 45 mmol) in ethyl acetate (150 mL) is degassed and 10% palladium on carbon (1 g) added. The reaction is evacuated and placed under 50 psi of hydrogen gas for 4 hours. Filtration of the reaction mixture through celite is followed by concentration of the filtrate to give 5-amino-2-acetoxyindane.

Step D. To a solution of the amine from Step C (1.44 g, 7.54 mmol) in methylene chloride (100 mL) and pyridine (0.73 mL, 9.05 mmol) at 0° C. is added 6-methyl-4'-trifluoromethyl-1,1'-biphenyl-2-carboxylic acid chloride (2.38 g, 8.0 mmol). The reaction mixture is stirred at room temperature overnight. The mixture is washed with 1N HCl, sodium bicarbonate and brine, dried over sodium sulfate, filtered and concentrated. The residue is crystallized from ethyl acetate/hexanes/ether to give 6-methyl-4'-trifluoromethyl-1,1'-biphenyl-N-(2-acetoxyindan-5-yl)]-2-carboxamide as a white solid.

Step E. To a solution of the amide from Step D (3.0 g, 6.62 mmol) in THF (50 mL) and methanol (20 mL) is added 1N NaOH (13.24 mL, 13.24 mmol). The reaction is stirred for 90 minutes, then concentrated in vacuo. The residue is extracted with ethyl acetate and the organic layer is washed with brine, dried over sodium sulfate, filtered, and concentrated in vacuo. Crystallization from ether/hexanes gives the 6-methyl-4'-trifluoromethyl-1,1'-biphenyl-N-(2-hydroxyindan-5-yl)-2-carboxamide.

Step F. To a solution of the alcohol from Step E (2.18 g, 5.3 mmol) in methylene chloride (50 mL) is added pyridinium dichromate (2.99 g, 7.95 mmol). The reaction is stirred for 17 hours. The mixture is filtered through florisil, then chromatographed on silica gel eluting with ethyl acetate/hexanes (1:2) to give 6-methyl-4'-trifluoromethyl-1,1'-biphenyl-N-(2-oxoindan-5-yl)-2-carboxamide as a white solid.

Step G. To a solution of the ketone from Step F (0.55 g, 1.35 mmol) in toluene (50 mL) is added p-toluenesulfonic acid (0.025 g, 0.13 mmol) and N-carbomethoxypiperazine (0.213 g, 1.46 mmol). The mixture is refluxed overnight with the removal of water using a Dean-Stark condenser. The mixture is poured into ethyl acetate, washed with 1N NaOH, brine, dried over magnesium sulfate, filtered and concentrated to give 6-methyl-4'-trifluoromethyl-1,1'-biphenyl-N-[2-[4-(methoxycarbonyl)-piperazino]-1H-inden-5-yl]-2-carboxamide.

Step H. To a solution of the compound from Step G (0.66 g, 1.23 mmol) in dichloroethane (10 mL) is added glacial acetic acid (0.71 mL, 1.23 mmol) followed by the addition of sodium triacetoxyborohydride (0.385 g, 1.73 mmol). The mixture is stirred overnight, poured into 1N NaOH, extracted with ethyl acetate, washed with brine, dried over magnesium sulfate, filtered and concentrated to give the desired racemic compound; mp 161–163° C.; MS (ES+), m/z 538 (M+1).

Prepared similarly to Example 1 are the following compounds:

| Example | Structure | MS [m/z] | MP (° C.) |
|---------|-----------|----------|-----------|
| 2 | 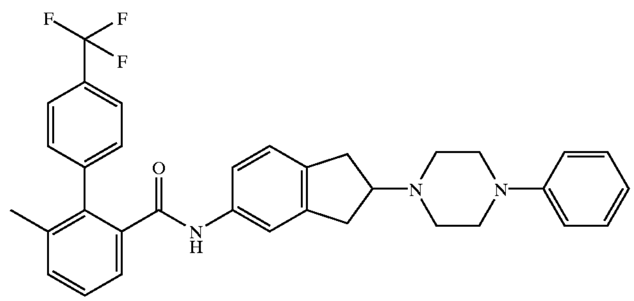 | 556 [M + 1] | 236–238 |
| 3 | 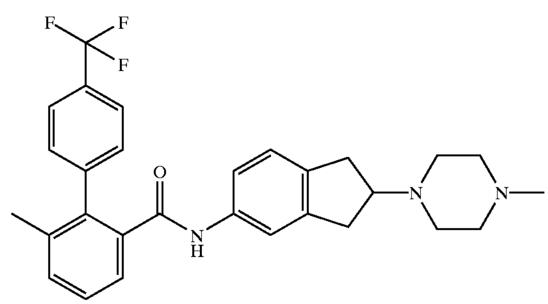 | 494 [M + 1] | 209–210 |
| 4 | 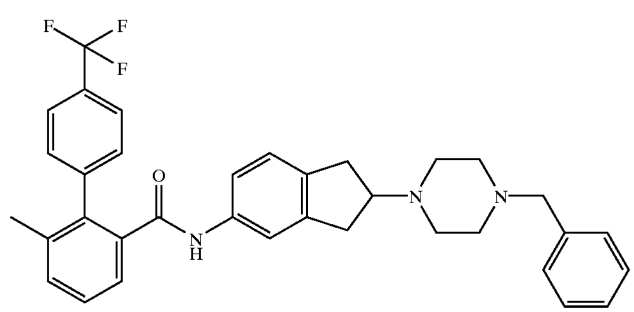 | 570 [M + 1] | 188–191 |
| 5 | 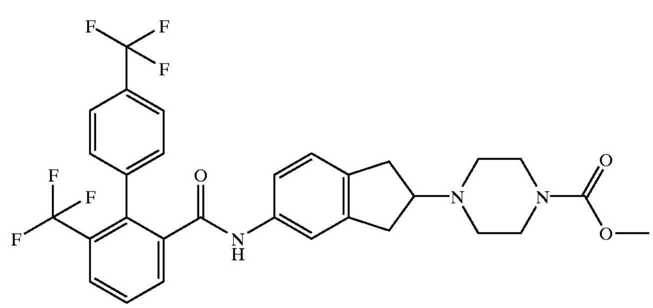 | 592 [M + 1] | 210–212 |

-continued

| Example | Structure | MS [m/z] | MP (° C.) |
|---------|-----------|----------|-----------|
| 6 | 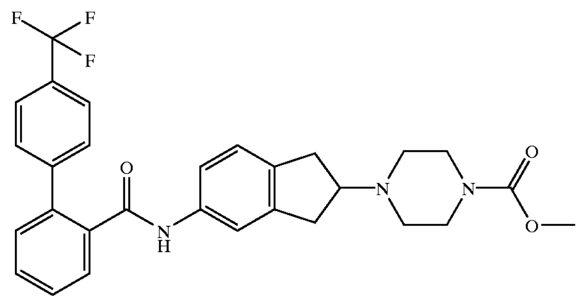 | 524 [M + 1] | 204–206 |
| 7 | 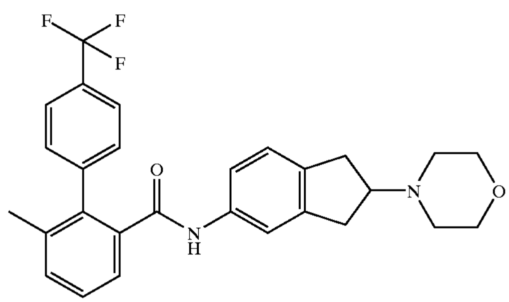 | 481 [M + 1] | 201–204 |
| 8 | 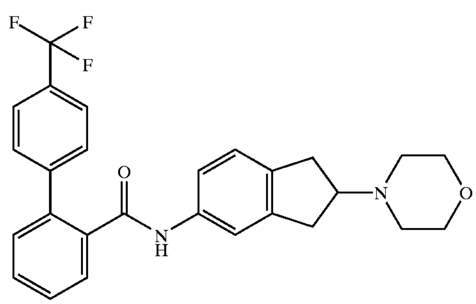 | 467 [M + 1] | 191–194 |
| 9 | 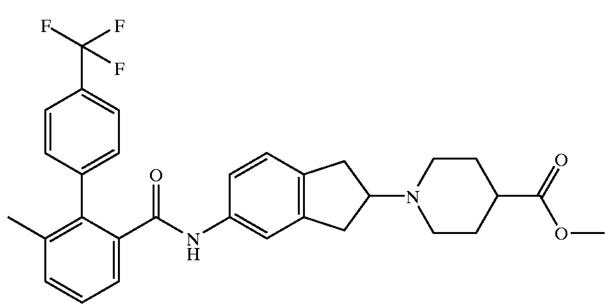 | 537 [M + 1] | 191–195 |
| 10 | 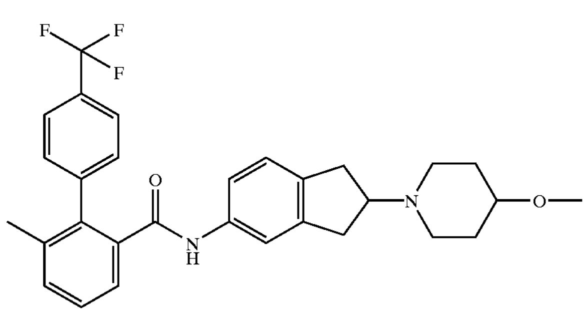 | 509 [M + 1] | 197–199 |

-continued

| Example | Structure | MS [m/z] | MP (° C.) |
|---|---|---|---|
| 11 | 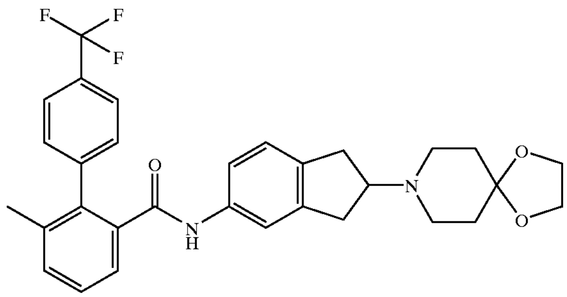 | 537 [M + 1] | 202–203 |
| 12 | 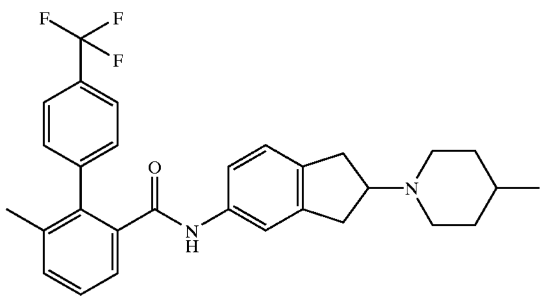 | 493 [M + 1] | 219–221 |
| 13 | 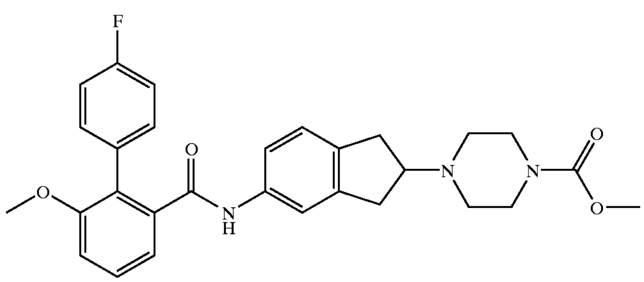 | 504 [M + 1] | 132–134 |

EXAMPLE 14

(R)-6-Methyl-4'-trifluoromethyl-1,1'-biphenyl-N-[2-[4-(methoxycarbonyl)-piperazino]indan-5-yl]-2-carboxamide

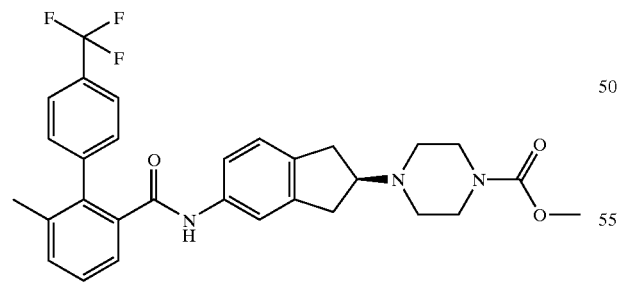

(R)-N-(2-aminoindan-5-yl)-6-methyl-4'-trifluoromethyl-1,1'-biphenyl-2-carboxamide (0.7 g, 1.7 mmole) is added to a solution of N,N-bis-(2-chloroethyl)-carbamic acid methyl ester (0.34 g, 1.7 mmole) in diisopropylamine (3 mL) at room temperature. The reaction mixture is heated to reflux for 3 hours, and evaporated to dryness. The residue is taken up in sodium bicarbonate solution and ethyl acetate. The organic layer is separated, dried over sodium sulfate and evaporated to dryness. The residue is chromatographed on silica gel eluting with ethyl acetate to give the title compound, m.p. 163–164° C.; $[\alpha]_D$–3.3 (c=10.12 mg/mL, DMSO), MS (ES+), m/z 538 (M+1).

The starting material N,N-bis-(2-chloroethyl)-carbamic acid methyl ester is prepared by treating a solution of bis-(2-chloroethyl)-amine hydrochloride in methylene chloride at 0° C. with methyl chloroformate (1.0 mole equivalent) and diisopropylethylamine (2.2 mole equivalents).

EXAMPLE 15

Similarly prepared to Example 14 is (S)-6-methyl-4'-trifluoromethyl-1,1'-biphenyl-N-[2-[4-(methoxycarbonyl)-piperazino]indan-5-yl]-2-carboxamide; mp 94–97° C.; $[\alpha]_D$+3.5 (c=5.0 mg/mL, DMSO), MS (ES+), m/z 538 (M+1), starting with (S)-6-methyl-4'-trifluoromethyl-1,1'-biphenyl-N-(2-aminoindan-5-yl)-2-carboxamide.

EXAMPLE 16

Similarly prepared to Example 14 is (R-)6-methyl-4'-trifluoromethyl-1,1'-biphenyl-N-[2-[4-(p-touenesulfonyl)-piperazino]indan-5-yl]-2-carboxamide; mp 129–130° C.; $[\alpha]_D$-28.33 (c=10.3 mg mL, DMSO); MS (ES+), m/z 634 (M+1).

The starting material, N,N-bis(2-chloroethyl)-p-toluenesulfonamide, is prepared by treating a solution of bis-(2-chloroethyl)-amine hydrochloride is methylene chloride at 0° C. with p-toluenesulfonyl chloride (1.0 mole equivalent) and diisopropylethylamine (2.2 mole equivalents).

EXAMPLE 17

6-Methyl-4'-trifluoromethyl-1,1'-biphenyl-N-(2-piperazinoindan-5-yl)-2-carboxamide

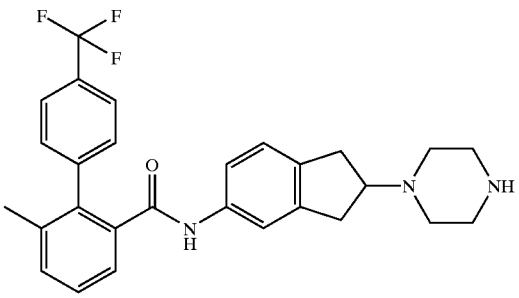

A solution of racemic 6-methyl-4'-trifluoromethyl-1,1'-biphenyl-N-[2-[4-(methoxycarbonyl)-piperazino]-indan-5-yl]-2-carboxamide (2.0 g, 3.72 mmol) is stirred with 33% HBr in acetic acid (20 mL) at room temperature overnight. The mixture is concentrated in vacuo, 1N NaOH is added and the mixture is extracted with ethyl acetate, the extract is washed with brine, dried over sodium sulfate, filtered and concentrated to give the title compound; m.p. 218–220° C.; MS (ES+) m/z 494 (M+1).

EXAMPLE 18

Prepared similarly to Example 17 is 4'-trifluoromethyl-1,1'-biphenyl-N-(2-piperazinoindan-5-yl)-2-piperazinoindan-5-yl)-2-carboxamide; mp 140° C. (foam); MS (ES+), m/z 466 (M+1).

EXAMPLE 19

Prepared similarly to Example 17 is (R)-6-methyl-4'-trifluoromethyl-1,1'-biphenyl-N-(2-piperazinoindan-5-yl)-2-carboxamide; m.p. 205–207° C.; $[\alpha]_D$-6.7 (c=10.6 mg/mL, DMSO).

EXAMPLE 20

A solution of 6-methyl-4'-trifluoromethyl-1,1'-biphenyl-N-[2-[4-(p-toluenesulfonyl)piperazino]indan-5-yl]-2-carboxamide (see Example 13) (0.686 g, 1.08 mol) is stirred with 33% HBr in acetic acid (4 mL) and phenol (0.306 mg, 3.25 mmol) at room temperature overnight. The mixture is concentrated in vacuo, azeotroped with toluene, and the residue triturated with ether. To the ether layer is added 1N NaOH and the mixture is extracted with ethyl acetate. The extract is washed with 1N NaOH, brine, dried over sodium sulfate, filtered and concentrated to give the compound of Example 14.

EXAMPLE 21

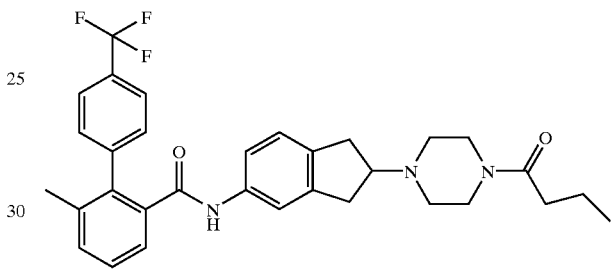

To a solution of compound of Example 17 (0.2 g, 0.417 mmol) in methylene chloride (10 mL) is added butyric anhydride (0.068 mL, 0.417 mmol) and diisopropyl amine (0.0727 mL, 0.417 mmol). The reaction is stirred overnight, washed with sodium bicarbonate, brine, dried over magnesium sulfate filtered and concentrated in vacuo. The residue is crystallized from ether to give 6-methyl-4'-trifluoromethyl-1,1'-biphenyl-N-[2-[(4-(1-oxobutyl)piperazino]indan-5-yl]-2-carboxamide; m.p. 173–176° C.; MS (ES+), m/z 550 (M+1).

Prepared similarly using the appropriate acylating agent are:

| Example | Structure | MS [m/z] | MP (° C.) |
|---|---|---|---|
| 22 | 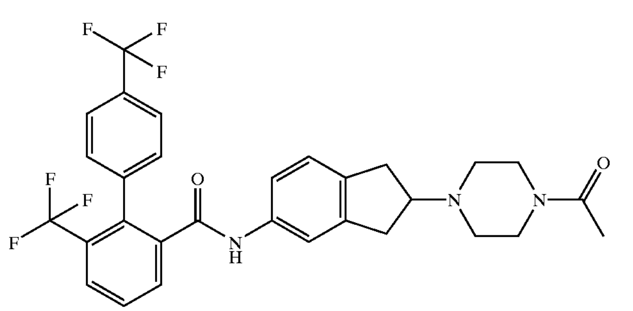 | 576 [M + 1] | 184–186 |

-continued

| Example | Structure | MS [m/z] | MP (° C.) |
|---|---|---|---|
| 23 | 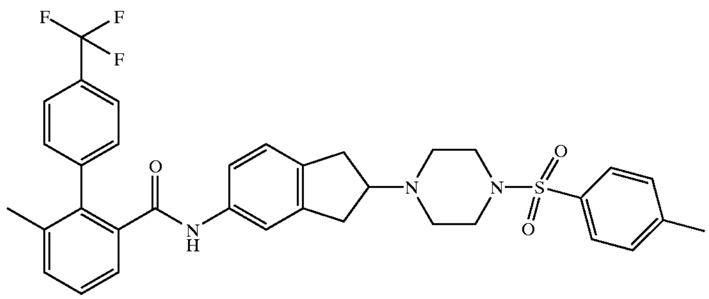 | 634 [M + 1] | 153–154 |
| 24 | 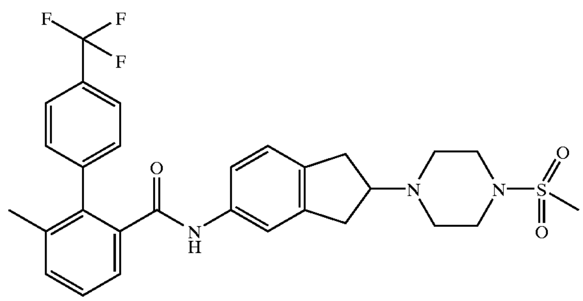 | 558 [M + 1] | 205–208 |
| 25 | 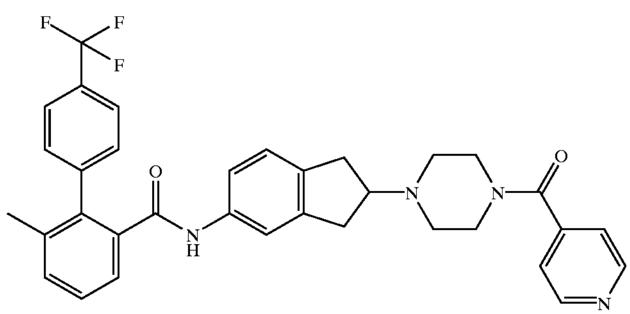 | 585 [M + 1] | 158–160 |
| 26 | 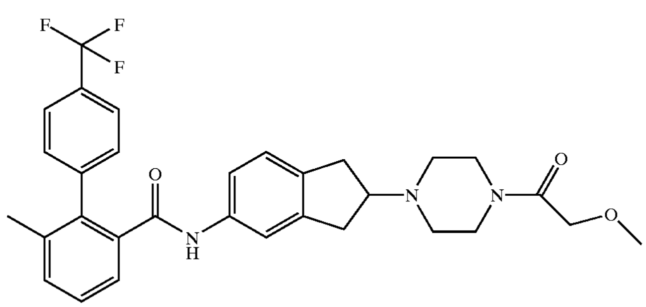 | 552 [M + 1] | 161–162 |
| 27 | 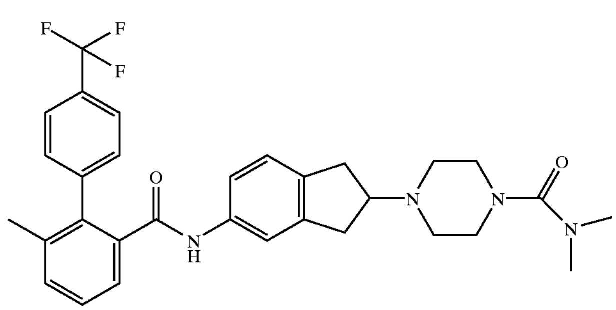 | 551 [M + 1] | 217–218 |

| Example | Structure | MS [m/z] | MP (° C.) |
|---|---|---|---|
| 28 | 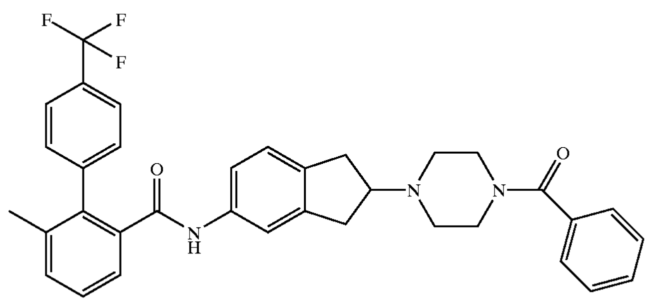 | 584 [M + 1] | 120–123 |
| 29 | 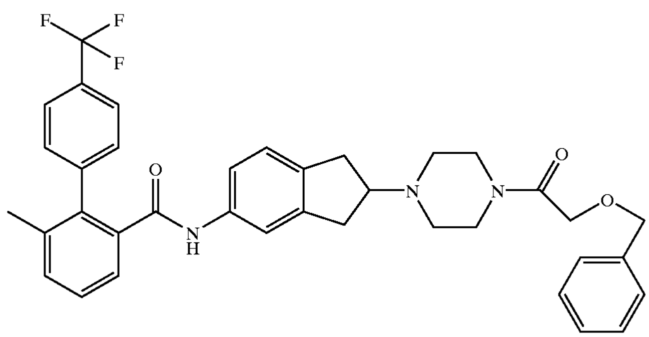 | 628 [M + 1] | 160–161 |
| 30 | 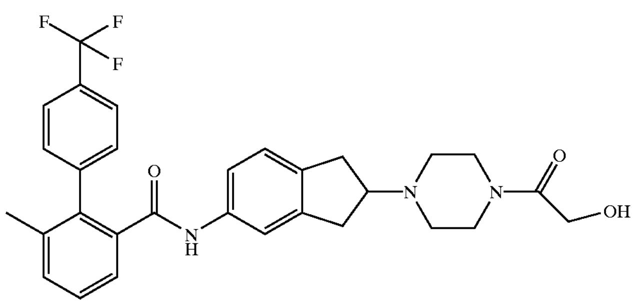 | 538 [M + 1] | 86–88 |

EXAMPLE 31

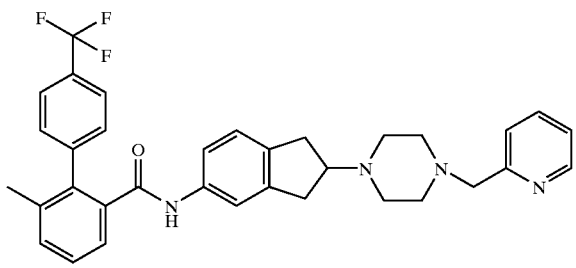

To a solution of compound of Example 17 (0.253 g, 0.528 mmol) in DMF (10 mL) is added potassium carbonate (0.145 g, 1.06 mmol) and 2-bromomethylpyridine (0.133 g, 0.53 mmol). The mixture is heated to 100° C. for 4 hours and stirred overnight at room temperature. The mixture is poured into brine and extracted with ethyl acetate. The extract is dried over magnesium sulfate, filtered, concentrated and the residue is chromatographed on silica gel eluting first with 3% methanol/methylene chloride, then 5% methanol/methylene chloride to give 6-methyl-4'-trifluoromethyl-1,1'-biphenyl-N-[2-[4-(2-pyridinylmethyl)piperazino]indan-5-yl]-2-carboxamide; mp 190–194° C.; MS (ES+), m/z 571 (M+1).

EXAMPLE 32

To a solution of compound of Example 17 (100 mg, 0.209 mmol), 2-bromopyridine (0.024 mL, 0.251 mmol), tris(dibenzylideneacetone)dipalladium (3.83 mg, 0.0042 mmol), and bis(diphenylphosphino)propane (3.45 mg, 0.0084 mmol) in 2 mL toluene is added sodium t-butoxide (48.2 mg, 0.502 mmol). The mixture is degassed and heated is an sealed tube at 120° C. for 17 hours. The mixture is poured into brine and extracted with ethyl acetate, dried over sodium sulfate, filtered, concentrated and chromatographed through silica gel eluting with ethyl acetate to give 6-methyl-4'-trifluoromethyl-1,1'-biphenyl-N-[2-[4-(2-pyridinyl)piperazino]-indan-5-yl]-2-carboxamide; mp 255–256° C.; MS (ES+), m/z 557 (M+1).

EXAMPLE 33

Prepared similarly to Example 32 is 6-methyl-4'-trifluoromethyl-1,1'-biphenyl-N-[2-[4-(4-pyridinyl)piperazino]-indan-5-yl]-2-carboxamide; mp 135–138° C.; MS (ES+), m/z 557 (M+1).

EXAMPLE 34

6-Methyl-4'-trifluoromethyl-1,1'-biphenyl-N-[7-[4-methoxycarbonyl)-piperazino]-6,7,8,9-tetrahydro-5H-benzocyclohepten-2-yl]-2-carboxamide

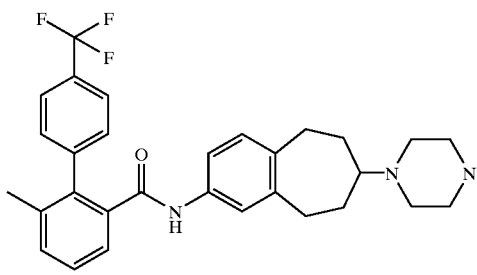

To 6,7,8,9-Tetrahydro-5H-benzocyclohepten-7-one (2.56 g, 16 mmol) and hydroxylamine hydrochloride (2.2 g, 32 mmol) in 27 mL of water is slowly added a solution of sodium carbonate (1.69 g, 16 mmol) in 14 mL of water. The mixture is stirred overnight. The solid is then filtered off, washed with water, and dried at 50° C. under reduced pressure to give 6,7,8,9-tetrahydro-N-hydroxy-5H-benzocyclohepten-7-amine as a white solid.

To a suspension of NaBH$_4$ (1.98 g, 52.3 mmol) in 40 mL of DME cooled in an ice-bath is added TiCl$_4$. To this mixture is added the above compound (2.3 g, 13.1 mmol) in 28 mL of DME dropwise. The mixture is stirred overnight, poured into ice water (135 mL), basified with 28% ammonia (20 mL) and extracted with ethyl acetate. The organic extracts are dried over magnesium sulfate, filtered and concentrated under reduced pressure to give 6,7,8,9-tetrahydro-5H-benzocyclohepent-7-amine as an oil.

The amine is treated with methyl chloroformate, nitrated, reduced and acylated with 6-methyl-4'-trifluoromethyl-1,1'-biphenyl-2-carboxylic acid chloride. The product is N-deprotected to the primary amine which is treated with N,N-bis(2-chloroethyl) carbamic acid methyl ester under conditions similar to those described above for indane derivatives to give the title compound.

EXAMPLE 35

2-(4-Trifluoromethylphenyl)-N-[2-[4-(methoxycarbonyl)-piperazino]indan-4-yl]-nicotinamide

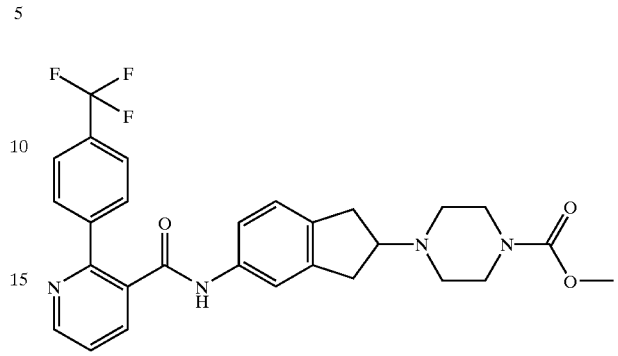

The title compound is prepared similarly to previous examples using 2-(4-trifluoromethyl-phenyl)-nicotinic acid chloride as starting material.

EXAMPLE 36

2-(4-trifluoromethylbenzyloxy)-3-methyl-N-[2[4-(methoxcarbonyl)-piperazino]-indan-5-yl]-benzamide

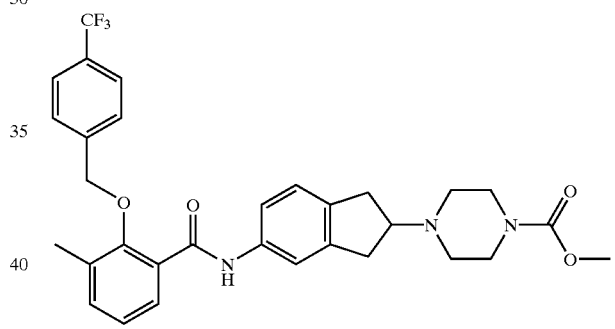

The title compound is prepared similarly to previous examples using 2-(4-trifluoromethylbenzyloxy)-3-methylbenzoic acid as starting material; mp 95–98° C.; MS (ES+), m/z 569 (M+1).

EXAMPLE 37–41

Prepared similarly to previous examples are:

| Example | Structure | MS [m/z] | MP (° C.) |
|---|---|---|---|
| 37 | 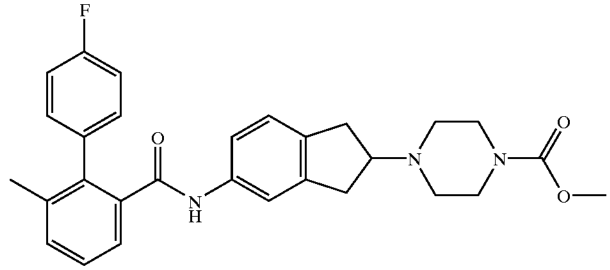 | 488 | 141–142 |

-continued

| Example | Structure | MS [m/z] | MP (° C.) |
|---------|-----------|----------|-----------|
| 38 | 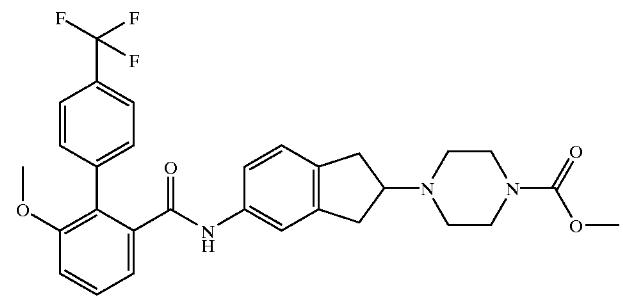 | 554 | 176–178 |
| 39 | 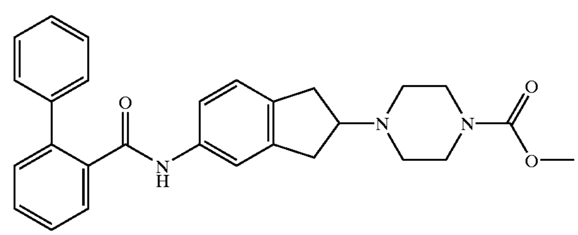 | 456 | 164–168 |
| 40 | 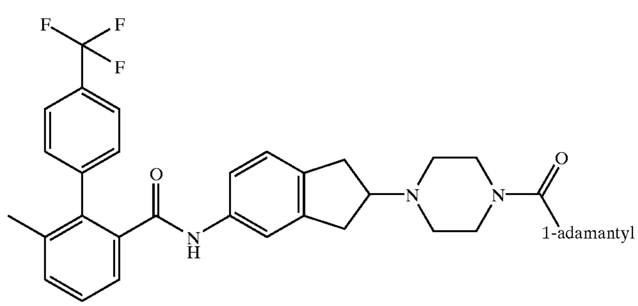 | 642 | 147–148 |
| 41 | 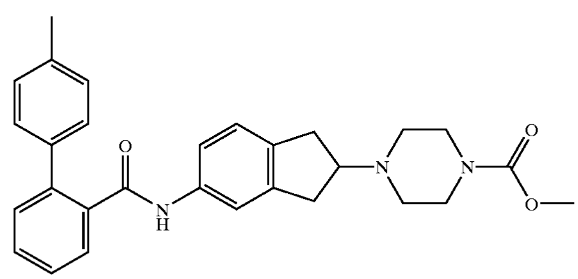 | 470 | 136–138 |

EXAMPLE 42

Hard gelatin capsules, comprising 50 mg active substance can be prepared, for example, as follows:

| Composition (for 1000 capsules) | |
|---|---|
| Active ingredient | 50.0 g |
| Lactose | 250.0 g |
| Microcrystalline cellulose | 30.0 g |
| Sodium Lauryl sulfate | 2.0 g |
| Magnesium stearate | 8.0 g |

The sodium lauryl sulfate is added to the active ingredient via a sieve with a mesh size of 0.2 mm. Both components are intimately mixed. Then first the lactose is added via a sieve with a mesh size of 0.6 mm and then the microcrystalline cellulose via a sieve with a mesh size of 0.9 mm. Thereupon these components are intimately mixed for a further 10 minutes. Finally the magnesium stearate is added via a sieve with a mesh size of 0.8 mm. After 3 minutes of further mixing, the formulation is filled into hard gelatin capsules of size 0 (340 mg each).

What is claimed is:

1. A compound of the formula

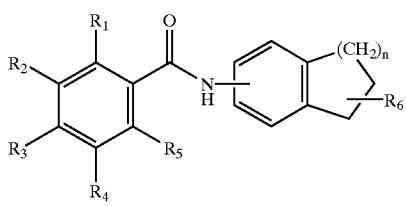

(I)

wherein n is 1, 2 or 3;

$R_1$ is aryl, heteroaryl or (aryl or heteroaryl)-lower alkoxy;

$R_2$, $R_3$, $R_4$ and $R_5$ are independently hydrogen, lower alkyl, lower alkoxy, halo, trifluoromethyl or cyano;

$R_6$ is

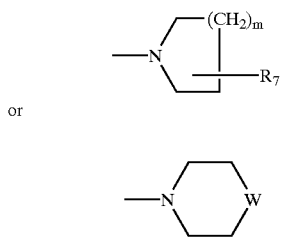

(i)

or (ii)

m is 1, 2 or 3;

$R_7$ is hydrogen, lower alkyl, (aryl or heteroaryl)-lower alkyl, lower alkoxy, (aryl or heteroaryl)-lower alkoxy, hydroxy, oxo, lower alkylenedioxy or lower alkanoyloxy;

W is O, S or

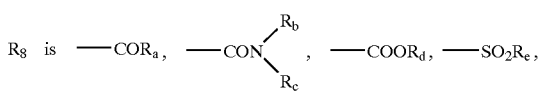

$R_8$ is —$COR_a$, —$CON\begin{smallmatrix}R_b\\R_c\end{smallmatrix}$, —$COOR_d$, —$SO_2R_e$, hydrogen, optionally substituted lower alkyl, aryl, heteroaryl or (aryl or heteroaryl)-lower alkyl;

$R_a$, $R_d$ and $R_e$ are independently optionally substituted lower alkyl, cycloalkyl, adamantyl, aryl, heteroaryl or (aryl or heteroaryl)-lower alkyl;

$R_b$ and $R_c$ are independently hydrogen, cycloalkyl, optionally substituted lower alkyl, aryl, heteroaryl or (aryl or heteroaryl)-lower alkyl; or $R_b$ and $R_c$ together represent lower alkylene; and in the above definitions heteroaryl represents monocyclic or bicyclic heterocyclic aryl selected from pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolyl, benzimidazolyl and benzofuryl, each optionally substituted by lower alkyl, lower alkoxy or halo, the point of attachment of said heterocycle being at a carbon atom of the heterocyclic ring; and optionally substituted lower alkyl represents lower alkyl or lower alkyl substituted by one or more groups selected from halo, $CF_3$, hydroxy, alkoxy, alkoxyalkoxy, aryloxy, cycloalkyl, alkanoyl, alkanoyloxy, amino, alkanoylamino, thiol and alkylthio;

or a pharmaceutically acceptable salt thereof; or an enantiomer thereof.

2. A compound according to claim 1 of the formula

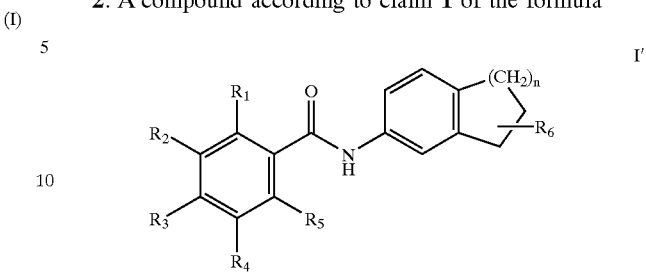

I' wherein n, and $R_1$–$R_6$ have meaning as defined in claim 1; or a pharmaceutically acceptable salt thereof; or an enantiomer thereof.

3. A compound according to claim 1 of the formula

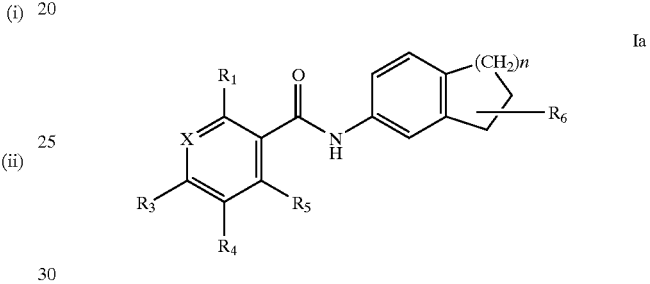

Ia wherein X is $R_2$—C; and n, and $R_1$–$R_6$ have meaning as defined in claim 1; a pharmaceutically acceptable salt thereof; or an enantiomer thereof.

4. A compound according to claim 3 of formula Ia wherein n is 1; $R_1$ is monocyclic aryl or heteroaryl; X is $R_2$—C; $R_2$, $R_3$, $R_4$ and $R_5$ are independently hydrogen, lower alkyl, halo, trifluoromethyl, lower alkoxy or cyano; $R_6$ is as defined in claim 3; a pharmaceutically acceptable salt thereof; or an enantiomer thereof.

5. A compound according to claim 3 of the formula

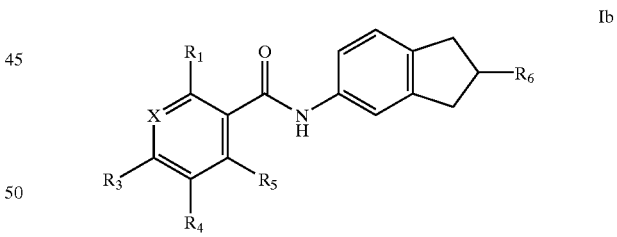

Ib wherein $R_1$ is monocyclic aryl or heteroaryl; X is $R_2$—C; $R_2$, $R_3$, $R_4$ and $R_5$ are independently hydrogen, lower alkyl, halo, trifluoromethyl, cyano or lower alkoxy; and $R_6$ has meaning as defined in claim 3; or a pharmaceutically acceptable salt thereof; or an enantiomer thereof.

6. A compound according to claim 5 of formula Ib wherein $R_1$ is phenyl or phenyl substituted by fluoro, chloro, trifluoromethyl, cyano or lower alkyl; X is $R_2$—C; $R_2$, $R_3$, $R_4$ and $R_5$ are independently hydrogen, lower alkyl, halo or trifluoromethyl; and $R_6$ is group of formula (i) wherein $R_7$ is (aryl or heteroaryl)-lower alkyl, lower alkoxy, (aryl or heteroaryl)-lower alkoxy, hydroxy, lower alkanoyloxy, oxo or lower alkylenedioxy, and m is 2; or $R_6$ is group of formula (ii) wherein W is $NR_8$; and $R_8$ is

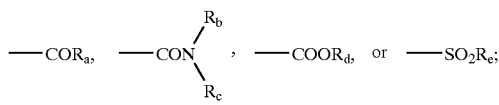

and $R_a$–$R_e$ have meaning as defined in claim 5, a pharmaceutically acceptable salt thereof; or an enantiomer thereof.

7. A compound according to claim 1 of the formula

Ic wherein $R_2$ is hydrogen, $C_1$–$C_4$-alkyl, $C_1$–$C_4$-alkoxy, trifluoromethyl, chloro or fluoro;

$R_8$ is —$COR_a$, —$CONR_bR_c$, —$COOR_a$ or —$SO_2Re$;

$R_a$—$R_e$ have meaning as defined in claim 1; and $R_9$ is trifluoromethyl, chloro or cyano; a pharmaceutically acceptable salt thereof; or an enantiomer thereof.

8. A compound according to claim 7 of formula Ic wherein $R_2$ is hydrogen, methyl or trifluoromethyl; $R_8$ is as defined in claim 7; $R_9$ is trifluoromethyl or chloro; a pharmaceutically acceptable salt thereof; or an enantiomer thereof.

9. A compound according to claim 7 of formula Ic wherein $R_2$ is methyl; $R_8$ is —$COOR_d$ wherein $R_d$ is lower alkyl; and $R_9$ is trifluoromethyl; a pharmaceutically acceptable salt thereof; or an enantiomer thereof.

10. A compound according to claim 5 of formula Ib′

Ib′ wherein $R_1$ is monocyclic aryl or heteroaryl; X is $R_2$—C; $R_2$, $R_3$, $R_4$ and $R_5$ are independently hydrogen, lower alkyl, halo, trifluoromethyl, cyano, or lower alkoxy; and $R_6$ has meaning as defined in claim 5; or a pharmaceutically acceptable salt thereof.

11. A compound according to claim 10 wherein X is $R_2$—C; $R_1$ is 4-trifluoromethylphenyl; $R_2$ is methyl; $R_3$–$R_5$ are hydrogen; and $R_6$ is (4-methoxycarbonyl)piperazino; or a pharmaceutically acceptable salt thereof.

12. A pharmaceutical composition comprising a compound of claim 1 and one or more pharmaceutically acceptable carriers.

13. A method for inhibiting microsomal triglyceride transfer protein in a mammal, for decreasing apolipoprotein B secretion in a mammal or for treating microsomal triglyceride transfer protein or apolipoprotein B dependent conditions in a mammal which comprises administering to a mammal in need thereof a correspondingly effective amount of a compound of claim 1.

14. A method according to claim 13 for treating atherosclerosis, hypertriglyceridemia or hypercholesteremia.

* * * * *